US007572953B2

(12) United States Patent
Cheng et al.

(10) Patent No.: US 7,572,953 B2
(45) Date of Patent: Aug. 11, 2009

(54) PLANTS WITH DELAYED FLOWERING

(75) Inventors: Xiaofei Cheng, Ardmore, OK (US); Zengyu Wang, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 282 days.

(21) Appl. No.: 11/211,148

(22) Filed: Aug. 24, 2005

(65) Prior Publication Data

US 2006/0059586 A1 Mar. 16, 2006

Related U.S. Application Data

(60) Provisional application No. 60/604,253, filed on Aug. 25, 2004.

(51) Int. Cl.
C12N 15/29 (2006.01)
C12N 15/82 (2006.01)
C12N 5/04 (2006.01)
A01H 5/00 (2006.01)
A01H 5/10 (2006.01)

(52) U.S. Cl. .................... 800/298; 536/23.1; 536/23.6; 435/320.1; 435/419; 435/468; 800/278; 800/290; 800/287

(58) Field of Classification Search ................ 536/23.1, 536/23.6; 435/320.1, 410, 419; 800/278, 800/298, 290, 287, 260
See application file for complete search history.

(56) References Cited

U.S. PATENT DOCUMENTS

2004/0034888 A1* 2/2004 Liu et al. .................... 800/289

FOREIGN PATENT DOCUMENTS

WO WO 96/14414 5/1996
WO WO 03/000904 1/2003

OTHER PUBLICATIONS

Bowie et al, Science 247:1306-1310, 1990.*
McConnell et al, Nature 411 (6838):709-713, 2001.*
MacDonald et al (2003, Cell 113:671-672).*
Cheng and Wang, "Overexpression of COL9, a Constans-Like gene, delays flowering by reducing expression of CO and FT in *Arabidopsis thaliana,*" *Plant J.*, 43(5):758-68, 2005.
Fowler et al. "Gigantea: a circadian clock-controlled gene that regulates photoperiodic flowering in *Arabidopsis* and encodes a protein with several possible membrane-spanning domains," *EMBO J.*, 18:4679-4688, 1999.
Griffiths et al., "The evolution of Constans-Like gene families in barley, rice, and *Arabidopsis,*" *Plant Physiol.*, 131:1855-1867, 2003.
Harmer et al., "Orchestrated transcription of key pathways in *Arabidopsis* by the circadian clock," *Science*, 290:2110-2113, 2000.
Hayama and Coupland, "Shedding light on the circadian clock and the photoperiodic control of flowering," *Curr. Opin. Plant Biol.*, 6(1):13-19, 2003.
Hayama et al., "Adaptation of photoperiodic control pathways produces short-day flowering in rice," *Nature*, 422(6933):719-722, 2003.
Hepworth et al., "Antagonistic regulation of flowering-time gene SOC1 by CPNSTANS and FLC via separate promoter motifs," *EMBO J.*, 21:4327-4337, 2002.
Hicks et al., "Early Flowering3 encodes a novel protein that regulates circadian clock function and flowering in *Arabidopsis,*" *Plant Cell*, 13:1281-1292, 2001.
Huq et al., "Gigantea is a nuclear protein involved in phytochrome signaling in *Arabidopsis,*" *Proc. Nat. Acad. Sci. USA*, 97:9789-9794, 2000.
Imaizumi et al., "FKF1 is essential for photoperiodic-specific light signalling in *Arabidopsis,*" *Nature*, 426:302-306, 2003.
Kardailsky et al., "Activation tagging of the floral inducer FT," *Science*, 286:1962-1965, 1999.
Kobayashi et al., "A pair of related genes with antagonistic roles in mediating flowering signals," *Science*, 286:1960-1962, 1999.
Koornneef et al., "A genetic and physiological analysis of late flowering mutants in *Arabidopsis thaliana,*" *Mol. Gen. Genet.*, 229:57-66, 1991.
Koornneef et al., "Genetic control of flowering time in *Arabidopsis,*" *Annu. Rev. Plant Physiol. Plant Mol. Biol.*, 49:345-370, 1998.
Ledger et al., "Analysis of the function of two circadian-regulated Constans-Like genes," *Plant Journal*, 26:15-22, 2001.
Lee et al., "The Agamous-Like 20 MADS domain protein integrates floral inductive pathways in *Arabidopsis,*" *Genes Dev.*, 14:2366-2376, 2000.
McWatters et al., "The ELF3 zeitnehmer regulates light signalling to the circadian clock," *Nature*, 408:716-720, 2000.
Michaels and Amasino, "Flowering Locus C encodes a novel MADS domain protein that acts as a repressor of flwoering," *Plant Cell*, 11:949-956, 1999.
Mizoguchi et al., "LHY and CCA1 are partially redundant genes required to maintain circadian rhythms in *Arabidopsis,*" *Dev. Cell*, 2:629-641, 2002.
Mouradov et al., "Control of flowering time: Interacting pathways as a basis for diversity," *Plant Cell*, S111-S130, 2002.
Nelson et al., "FKF1, a clock-controlled gene that regulates the transition to flowering in *Arabidopsis,*" *Cell*, 101:331-340, 2000.
Onouchi et al., "Mutagenesis of plants overexpressing Constans demonstrates novel interactions among *Arabidopsis* flowering-time genes," *Plant Cell*, 12:885-900, 2000.
Park et al., "Control of circadian rhythms and photoperiodic flowering by *Arabidopsis gigantea* gene," *Science*, 285:1579-1582, 1999.
Putterill et al., "The Constans gene of *Arabidopsis* promotes flowering and encodes a protein showing similarities to zinc finger transcription factors," *Cell*, 80:847-857, 1995.

(Continued)

*Primary Examiner*—Stuart F. Baum
(74) *Attorney, Agent, or Firm*—Sonnenchein Nath & Rosenthal LLP

(57) ABSTRACT

The invention provides plants with delayed flowering and methods of making such plants. Also provided are constructs comprising nucleic acids for making these plants. The invention is significant in that plants with delayed flowering may exhibit increased nutritional value and cold tolerance. Delayed flowering will also find use in plant breeding methods.

19 Claims, 13 Drawing Sheets

OTHER PUBLICATIONS

Reeves and Coupland, *Curr. Opin. Plant Biol.*, 3(1):37-42, 2000.

Robson et al., "Functional importance of conserved domains in the flowering-time gene Constans demonstrated by analysis of mutant alleles and transgenic plants," *Plant J.*, 28:619-631, 2001.

Samach et al., "Distinct roles of Constans target genes in reproductive development of *Arabidopsis*," *Science*, 288:1613-1616, 2000.

Scortecci et al., "Identification of a MADS-box gene, Flowering Locus M, that represents flowering," *Plant J.*, 26:229-236, 2001.

Searle and Coupland, "Induction of flowering by seasonal changes in photoperiod," *EMBO J.*, 23(6):1217-1222, 2004.

Simpson and Dean, "*Arabidopsis*, the Rosetta stone of flowering time?" *Science*, 296:285-289, 2002.

Simpson et al., "Evolution of flowering in response to day length: flipping the Constans switch," *Bioessays*, 25:829-832, 2003.

Simpson et al., "FY is an RNA 3' end-processing factor that interacts with FCA to control the *Arabidopsis* floral transition," *Cell*, 113(6):777-787, 2003.

Strayer et al., "Cloning of the *Arabidopsis* clock gene TOC1, an autoregulatory response regulator homolog," *Science*, 289:768-771, 2000.

Suarez-Lopez et al., "Constans mediates between the circadian clock and the control of flowering in *Arabidopsis*," *Nature*, 410:1116-1120, 2001.

Takada and Goto, "Terminal Flower2, an *Arabidopsis* homolog of Heterchromatin Protein1, counteracts the activation of Flowering Locus T by Constans in the vascular tissue of leaves to regulate flowering time," *Plant Cell*, 15:2856-2865, 2003.

Valverde et al., "Photoreceptor regulation of Constans protein in photoperiodic flowering," *Science*, 303:1003-1006, 2004.

Wang and Tobin, "Constitutive expression of the Carcadian Clock Associated 1 (CCA1) gene disrupts circadian rhythms and suppresses its own expression," *Cell*, 93:1207-1217, 1998.

Wang et al., "Characterization of cis-acting elements regulating transcription from the promoter of a constitutively active rice actin gene," *Molecular and Cellular Biology*, 12(8):3399-3406, 1992.

Yanovsky and Kay, "Molecular basis of seasonal time measurement in *Arabidopsis*," *Nature*, 419:308-312, 2002.

Database Genseq, "Plant full length insert polypeptide seqid 41685," Accession No. ADX72319, 2005.

Database Uniprot, "Zinc finger protein constans-like 9," Accession No. UNIPROT: COL9_ARATH, 2000.

\* cited by examiner

PLANTS WITH DELAYED FLOWERING

This application claims the priority of U.S. Provisional Patent Appl. Ser. No. 60/604,253, filed Aug. 25, 2004, the entire disclosure of which is specifically incorporated herein by reference.

BACKGROUND OF THE INVENTION

1. Field of the Invention

The present invention relates generally to the field of molecular biology. More specifically, the invention relates to modification of plant flowering and associated phenotypes.

2. Description of the Related Art

The transition of vegetative growth to reproductive growth in plants is controlled both by endogenous signals and environmental stimuli. Genetic and molecular dissections of flowering time mutants in *Arabidopsis* have identified four major pathways: photoperiod pathway, autonomous pathway, gibberellin pathway and vernalization pathway (Koornneef et al., 1991, 1998; Levy and Dean, 1998). A photoperiod promotion pathway affects flowering in long days, with mutants in this pathway flowering late under long-day (LD) conditions but not late flowering in short-day (SD) conditions.

The gibberellin pathway promotes flowering response to gibberellic acid (GA) signals and mutation of genes in the GA synthesis and signaling pathway delays flowering, especially under SD conditions. Mutants in the autonomous pathway and vernalization pathway flower late under both LD and SD conditions, showing a strong response to extended low temperature by suppression of FLOWERING LOCUS C (FLC). These different floral promotion pathways are integrated by a small set of genes, called integrators, which include FLOWERING LOCUS T (FT), SUPPRESSOR OF OVEREXPRESSION OF CO (SOC1), and LEAFY (LFY), forming an intricate flowering time control network (Lee et al., 2000; Mouradov et al., 2002; Simpson and Dean, 2002).

The photoperiod pathway mediates light and temporal environmental information into flowering time regulation. It comprises three parts: photoreceptors, a circadian clock and an output pathway from the clock specific to flowering (Simpson, 2003). Light is perceived by phytochromes (PHY) A through E and cryptochromes (CRY) 1 and 2, while the duration of the day and night is measured by the circadian clock (Simpson and Dean, 2002). CIRCADIAN CLOCK ASSOCIATED1 (CCA1), TIMING OF CHLOROPHYLL A/B BINDING PROTEIN1 (TOC1) and LATE ELONGATED HYPOCOTYL (LHY) are candidate genes that have been associated with the central oscillator of the circadian clock (Mouradov et al., 2002; Hayama and Coupland, 2003).

CONSTANS (CO) plays a central role in the photoperiod response pathway by mediating between the circadian clock and the floral integrators (Suárez-López et al., 2001; Searle and Coupland, 2004). CO is a transcription factor that promotes flowering time by inducing the expression of downstream genes FT (Kardailsky et al., 1999; Kobayashi et al., 1999; Onouchi et al., 2000; Samach et al., 2000) and SOC1 (Lee et al., 2000). Mutants of co exhibit a delayed flowering response under long-day (LD) but not short-day (SD) conditions (Koornneef et al., 1991; Putterill et al., 1995). Under LD conditions CO mRNA peaks in the evening and staying high until the following dawn, whereas under SD the mRNA peaks during the night (Suárez-López et al., 2001). This temporal pattern of CO expression provides a basis for the regulation of the pathway by day length (Searle and Coupland, 2004). The elevated CO mRNA level and the subsequently elevated protein level, which is stabilized by PHYA and CRY2 at late daytime, activate FT expression to promote flowering in LD (Yanovsky and Kay, 2002; Valverde et al., 2004). It has also been shown that key regulatory genes for the photoperiodic control of flowering are conserved between *Arabidopsis*, a LD plant, and rice, a SD plant, but regulation of FT by CO was reversed, resulting in the suppression of flowering in rice under LD conditions (Hayama et al., 2003; Simpson, 2003).

CO is a member of an *Arabidopsis* gene family with 16 other members (Robson et al., 2001). The family consists of putative transcription factors with two conserved domains (Putterill et al., 1995; Robson et al., 2001; Griffiths et al., 2003). The first is a zinc finger region near the amino terminus that resembles B-boxes, which is supposed to regulate protein-protein reactions. The second is the CCT (CO, CO-like, TOC1) domain near the carboxyl terminus, which is involved in nuclear localization of the proteins (Robson et al., 2001; Griffiths et al., 2003). Based on the variation of zinc finger region, the family is divided into three subgroups: group I includes CO and COL1 to COL5 with two zinc finger boxes; group II has COL6-COL8 and COL16 with one B-box; group III includes COL9 to COL15 with one B-box and a second diverged zinc finger (Robson et al., 2001).

COL9 (At3g07650, named COL11 in the TIGR Gene Indices)) is a CO-like gene the cDNA of which contains 3 introns and 4 exons and encodes a protein of 372 amino acids. The gene belongs to group III. Its amino acid sequence shares 48.5% identity in B-box region and 62% identity in CCT domain with CO. However, the function of COL9 has been unknown and has not been analyzed in vivo.

Beside CO, COL1 and COL2 are the other two characterized genes in the family. The expression of COL1 and COL2 is also regulated by circadian clock with an expression peak at dawn, but the altered expression of COL1 and COL2 had little effect on flowering time (Ledger et al., 2001). The functions of the other members in this family are largely unknown.

While the studies to date have provided a further understanding of plant flowering generally, the function of many CO-related genes remains to be determined. Effective techniques for the lengthening of flowering time in particular have thus far been lacking. There is, therefore, a great need in the art for novel methods and compositions for delaying flowering in plants. Such methods could yield plants with significantly improved nutrition and aid farmers and consumers alike.

SUMMARY OF THE INVENTION

In one aspect, the invention provides an isolated nucleic acid sequence encoding COL9, wherein the nucleic acid sequence is operably linked to a heterologous promoter. In certain embodiments, the nucleic acid is further defined as selected from the group consisting of: (a) a nucleic acid sequence encoding the polypeptide of SEQ ID NO:2; (b) a nucleic acid sequence comprising the sequence of SEQ ID NO:1; (c) a nucleic acid sequence hybridizing to SEQ ID NO 1 under conditions of 5×SSC, 50% formamide and 42° C.; and (d) a nucleic acid sequence encoding a polypeptide with at least 50% sequence identity to SEQ ID NO:2. In another embodiment, the nucleic acid is further defined as a nucleic acid sequence encoding a polypeptide with at least 90% sequence identity to SEQ ID NO:2. In another embodiment, the nucleic acid sequence is further defined as selected from the group consisting of: (a) a nucleic acid sequence encoding the polypeptide encoded by SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32 or SEQ ID NO:33; (b) a nucleic acid sequence comprising the sequence of SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32 or SEQ ID NO:33; (c) a nucleic acid sequence hybridizing under conditions of 5×SSC, 50% formamide and 42° C. to SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32 or SEQ ID NO:33; and (d) a nucleic acid sequence encoding a polypeptide with at least 90% sequence identity to the polypeptide encoded by SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32 or SEQ ID NO:33.

In another aspect, the invention provides an isolated nucleic acid sequence encoding COL10, wherein the nucleic acid sequence is operably linked to a heterologous promoter. In certain embodiments, the nucleic acid is further defined as selected from the group consisting of: (a) a nucleic acid sequence encoding the polypeptide of SEQ ID NO:35; (b) a nucleic acid sequence comprising the sequence of SEQ ID NO:34; (c) a nucleic acid sequence hybridizing to SEQ ID NO 34 under conditions of 5×SSC, 50% formamide and 42° C.; and (d) a nucleic acid sequence encoding a polypeptide with at least 50% sequence identity to SEQ ID NO:35. In another embodiment, the nucleic acid is further defined as a nucleic acid sequence encoding a polypeptide with at least 90% sequence identity to SEQ ID NO:35.

In another aspect, the invention provides a recombinant vector comprising an isolated nucleic acid sequence according to the invention. The recombinant vector may further comprise at least one additional sequence chosen from the group consisting of: a regulatory sequence, a selectable marker, a leader sequence and a terminator. The additional sequence may be a heterologous sequence. The promoter may be a developmentally-regulated, organelle-specific, inducible, tissue-specific, constitutive, cell-specific, seed specific, or germination-specific promoter. In one embodiment the recombinant vector may be defined as an isolated expression cassette.

In yet another aspect, the invention provides a transgenic plant transformed with a selected DNA comprising a nucleic acid sequence of the invention. The plant may be defined as a monocotyledonous or dicotyledonous plant. The plant may be an $R_0$ transgenic plant and may be a progeny plant of any generation of an $R_0$ transgenic plant, wherein said transgenic plant has inherited said selected DNA from said $R_0$ transgenic plant.

In still yet another aspect, the invention provides a seed of a transgenic plant of the invention, wherein the seed comprises the specified selected DNA. The invention also provides a host cell transformed with a selected DNA comprising a nucleic acid sequence of the invention. Such a cell may express a protein encoded by the selected DNA. The cell may have inherited the selected DNA from a progenitor of the cell and may have been transformed directly with the selected DNA. In one embodiment the host cell is a plant cell.

In still yet another aspect, the invention provides a method of delaying flowering in a plant comprising introducing into the plant an isolated nucleic acid sequence of the invention encoding COL9, or COL10, wherein the nucleic acid is expressed in the plant to delay flowering relative to a plant of the same genotype that lacks the isolated nucleic acid. In the method the nucleic acid sequence may be from a species selected from the group consisting of: *Arabidopsis thaliana*, barley, cotton, grape, maize, potato, rice, sugarcane, sorghum, soybean, tomato, wheat and *Medicago truncatula*. In one embodiment, the nucleic acid is further defined as selected from the group consisting of: (a) a nucleic acid sequence encoding the polypeptide of SEQ ID NO:2 or SEQ ID NO:35; (b) a nucleic acid sequence comprising the sequence of SEQ ID NO:1 or SEQ ID NO:34; (c) a nucleic acid sequence hybridizing to SEQ ID NO 1 or SEQ ID NO:34 under conditions of 5×SSC, 50% formamide and 42° C.; and (d) a nucleic acid sequence encoding a polypeptide with at least 50% sequence identity to SEQ ID NO:2 or SEQ ID NO:35. In another embodiment, the nucleic acid is further defined as a nucleic acid sequence encoding a polypeptide with at least 90% sequence identity to SEQ ID NO:2 or SEQ ID NO:35. In another embodiment, the nucleic acid sequence is defined as selected from the group consisting of: (a) a nucleic acid sequence encoding the polypeptide encoded by SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32 or SEQ ID NO:33; (b) a nucleic acid sequence comprising the sequence of SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32 or SEQ ID NO:33; (c) a nucleic acid sequence hybridizing under conditions of 5×SSC, 50% formamide and 42° C. to SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32 or SEQ ID NO:33; and (d) a nucleic acid sequence encoding a polypeptide with at least 90% sequence identity to the polypeptide encoded by SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32 or SEQ ID NO:33. In certain embodiments, introducing the isolated nucleic acid comprises plant breeding or genetic transformation.

In still yet another aspect, the invention provides a method of making food for human or animal consumption comprising: (a) obtaining a transgenic plant in accordance with the invention; (b) growing the plant under plant growth conditions to produce plant tissue from the plant; and (c) preparing food for human or animal consumption from said plant tissue. In the method, preparing food may comprise harvesting said plant tissue. In certain embodiments the food is starch, protein, meal, flour or grain.

In still yet another aspect, the invention provides a method of plant breeding comprising: (a) obtaining a first transgenic plant provided by the invention comprising a sequence encoding COL9 or COL10 and a second plant; (b) growing the first and second plants to sexual maturity; and (c) allowing pollen from the first plant to pollinate a flower on the second plant or pollen from the second plant to pollinate a flower on the first plant to produce a hybrid progeny seed of the first and second plants.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

DETAILED DESCRIPTION OF THE INVENTION

Figure 1:
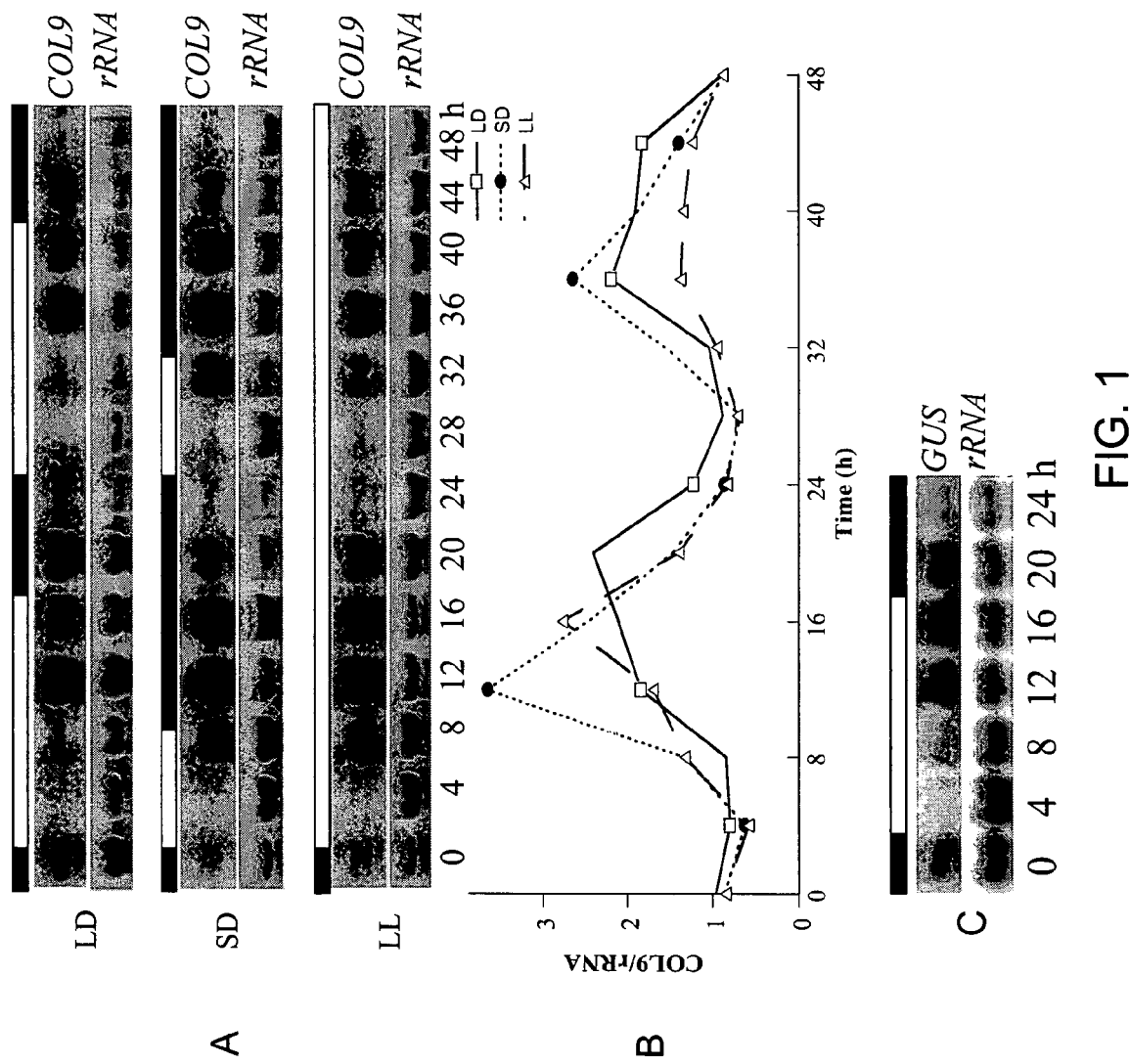
FIG. 1. Analysis of COL9 expression pattern in wild-type and transgenic plants by northern hybridization. (A) COL9 mRNA accumulation in wild-type plants under LD, SD and LL conditions. LD: 16 h light/8 h dark; SD: 8 h light/16 h dark; LL: continuous light. (B) Quantification of COL9 mRNA abundance from the northern blots shown in (A). (C) Accumulation of GUS mRNA in transgenic plants carrying GUS gene driven by the COL9 promoter (COL9::GUS).

The invention overcomes the limitations of the prior art by providing methods and compositions for the delaying of flowering in plants. This is significant because the decline of nutritive value in forages such as grasses or legumes is associated with the onset of stem growth and flowering. Delaying the formation of less digestible stems and delaying the flowering process will therefore find use in increased forage and food quality. The invention will be of particular benefit in forage crops, as well as staple crops including wheat and rye. In forage crops, delayed flowering will not only help to prolong grazing time, but may also be used in the improvement of early flowering lines, which generally have good fall growth, to escape freezing. Persistence in particular may be improved in plants with delayed flowering based on increased use of roots as the major sink rather than stems and flowers.

Delayed flowering will also find use in plant breeding, for example, in aiding hybrid seed production in species such as maize. In one embodiment, delayed flowering may be used such that pollen from a plant is not available at the same time that flowers on the same plant are receptive to the pollen. Self-pollination that naturally otherwise occurs can be avoided in this way. Pollen from other plants may then be made available for the production of hybrid seed.

The inventors showed, surprisingly, that heterologous expression of the Constans-like gene COL9 originally isolated from Arabidopsis resulted in delayed flowering under long day conditions, while cosuppression lines and a T-DNA insertion line showed somewhat earlier flowering under these conditions. This is significant and surprising because overexpression of CONSTANS (CO) promotes plant flowering. COL9 was shown by the inventors to be regulated by a circadian clock in the photoperiod pathway, with GUS expression under the control of a COL9 promoter detected in different organs throughout development. The results indicated that COL9 regulates flowering time by modulating the expression of CO as well as the integrator gene FT in the photoperiod pathway.

The invention therefore provides plant transformation constructs comprising a COL9 coding sequence and plants transformed therewith. Exemplary coding sequences for use with the invention include the *Arabidopsis thaliana* COL9 coding sequence (SEQ ID NO:1). Such coding sequences may encode a polypeptide having the amino acid sequence of SEQ ID NO:2. COL9 homologs may also find use with the invention, including homologs from wheat, barley, cotton, lollium, maize, Medicago, potato, rice, sorghum, soybean and tomato (SEQ ID Nos:23-33, respectively).

A COL9 coding sequence used in accordance with the invention may be from a monocot or dicot plant, including any of the foregoing species, as described herein. Sequences that hybridize under stringent conditions to the COL9 coding sequences provided by the invention are also provided by the invention. An example of such conditions is 5×SSC, 50% formamide and 42° C. It will be understood by those of skill in the art that stringency conditions may be increased by increasing temperature, such as to about 60° C. or decreasing salt, such as to about 1×SSC, or may be decreased by increasing salt, for example to about 10×SSC, or decreasing temperature, such as to about 25° C.

Nucleic acids provided by the invention include those encoding active COL9 fragments. Those of skill in the art will immediately understand in view of the current disclosure that such fragments may be prepared by placing fragments of COL9 coding sequences in frame in an appropriate expression vector, for example, comprising a plant promoter. Polypeptides may also readily be fragmented and assayed for activity. Using the assays described in the working examples, COL9 activity can be efficiently confirmed for any given fragment. Fragments of nucleic acids, for example, may be prepared according to any of the well known techniques including partial or complete restriction digests and physical shearing, for example, by sonication.

Sequences provided by the invention may be defined as encoding an active COL9. Coding sequences may be provided operably linked to a heterologous promoter, in either sense or antisense orientation. Expression constructs are also provided comprising these sequences, including antisense oligonucleotides thereof, as are plants and plant cells transformed with the sequences.

I. Plant Transformation Vectors

The construction of vectors which may be employed in conjunction with plant transformation techniques using the COL9 coding sequences provided by the invention will be known to those of skill of the art in light of the present disclosure (see, for example, Sambrook et al., 2001; Gelvin et al., 1990). The techniques of the current invention are thus not limited to any particular nucleic acid sequences.

One important use of the sequences provided by the invention will be in the alteration of plant phenotypes by genetic transformation with COL9 coding sequences. The COL9 coding sequence may be provided with other sequences and may be in sense or antisense orientation with respect to a promoter sequence. The choice of any additional elements used in conjunction with an COL9 coding sequences will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of a COL9 coding sequence is used. In other embodiments, a heterologous promoter is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that COL9 coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of a COL9 coding sequence is used. Alternatively, a heterologous 3' end may enhance the expression of sense or antisense COL9 coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens,* and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

E. Antisense Constructs

Antisense treatments represent one way of altering COL9 activity in accordance with the invention. In particular, constructs comprising a COL9 coding sequence, including fragments thereof, in antisense orientation, may be used to decrease or effectively eliminate the expression of COL9 in a plant. Accordingly, this may be used to shorten flowering in a plant. As such, antisense technology may be used to "knockout" the function of a COL9 coding sequence or homologous sequences thereof.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject. In certain embodiments of the invention, such an antisense oligonucleotide may comprise any unique portion of a nucleic acid sequence provided herein. In certain embodiments of the invention, such a sequence comprises at least 18, 30, 50, 75 or 100 or more contiguous nucleic acids of the nucleic acid sequence of SEQ ID NO:1, which may be in sense/and or antisense orientation. By including sequences in both sense and antisense orientation, increased suppression of the corresponding coding sequence may be achieved.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

II. Genetic Transformation

Suitable methods for transformation of cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

Agrobacterium-mediated transfer is one widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is typically the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Electroporation may also be used to transform plants. In this instance it may be desired to employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

Transformation of protoplasts can be achieved using methods based on calcium, phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar, Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

DNA is generally introduced into only a small percentage of target cells in any one transformation study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318).

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468; each of the disclosures of which is specifically incorporated herein by reference in its entirety).

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}M$ abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected COL9 coding sequence can be introduced into a plant variety by crossing, without the need for ever directly transforming a plant of that variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VI. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

COL9 is a Circadian Clock Regulated and Nuclei-Localized Gene with Distinct Transcript Expression Peak Under Long Day and Short Day Conditions The temporal expression pattern of COL9 was analyzed using samples collected from *Arabidopsis* plants growing under short day and long day conditions. Northern hybridization was used for the analysis as described in Example 9 below. The analysis showed that, in contrast to CO, for which transcripts are rare and not detectable by northern analysis (Putterill et al., 1995), the transcript level of COL9 was abundant and could be easily detected by northern hybridization analysis (FIG. 1).

A robust cycling of COL9 transcript during the day was observed when the COL9 cDNA was used to probe the total RNA extracted from *Arabidopsis* leaves (FIG. 1A, B). Under long day conditions, the abundance COL9 mRNA was low after 4 h and 8 h of light entrance, and increased at 12 h with an expression peak at night time (FIG. 1A, B). Under short day conditions, COL9 transcript abundance was also detected as low at daytime and increasing around dusk with the expression peak at the beginning of the dark period (FIG. 1A, B). The lowest COL9 transcript point was at 4 hours after light entrance in both long day and short day conditions. The peak level of COL9 transcript was higher in plants growing in short days than plants growing in long days (FIG. 1B).

When transferred from short day to continuous light, the transcripts of COL9 showed a diurnal rhythm with reduced amplitude (FIG. 1A, B). The results indicate that COL9 expression is under the control of a circadian clock. Analysis was therefore carried out on the upstream genomic sequence of the COL9 gene to look for evidence of circadian clock regulation in the promoter region. Sequence analysis revealed the presence of 3 evening element motifs in the 1.3 kb promoter region of COL9 genomic sequences. This evening element motif (AAATATCT), has been shown to play an important role in conferring circadian rhythmicity in plants (Harmer et al., 2000).

A 1.3 kb promoter region of COL9 was next fused in frame with GUS and the chimeric gene construct (COL9::GUS) used to generate transgenic *Arabidopsis* plants, as described in Example 9 below. Northern hybridization revealed that under the control of COL9 promoter, GUS transcripts showed a similar diurnal rhythm as COL9 transcripts (FIG. 1C). The results further confirmed that COL9 is a circadian clock regulated gene.

Figure 2:
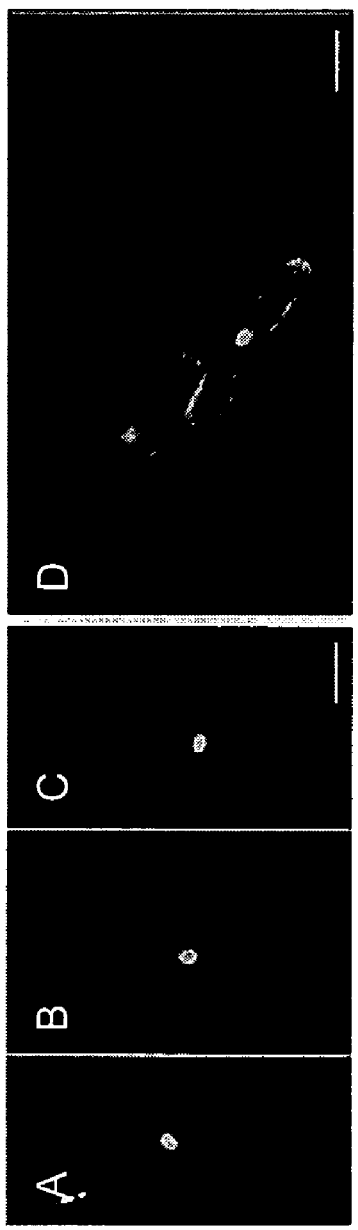
FIG. 2. Localization of GFP-COL9 fusion protein. (A-C) Transient GFP expression in onion epidermal cells by particle bombardment with plasmid 35S::GFP-COL9. (D) Transient GFP expression in onion epidermal cells by particle bombardment with plasmid 35S::GFP as control.

The presence of the CCT domain in the C terminus of COL9 indicated that the protein is localized in the nucleus. To confirm that COL9 is a nuclear protein, a translational fusion of sGFP and COL9 (35S::sGFP:COL9) was constructed under the control of a CaMV 35S promoter. A transient expression assay in onion epidermal cells was used to assess the cellular location of the fusion protein. In the bombarded cells expressing the fusion protein (GFP:COL9), GFP fluorescence was detected only in the nuclei (FIG. 2A-C); whereas in cells expressing free sGFP, GFP fluoresce was detectable in both the nuclei and the cytoplasm (FIG. 2D). Therefore, it was shown that the COL9 protein is localized in the nucleus; which is consistent with its deduced role in the transcriptional regulation of gene expression.

Example 2

COL9 is Expressed in Different Tissues and at Different Developmental Stages

Figure 3:
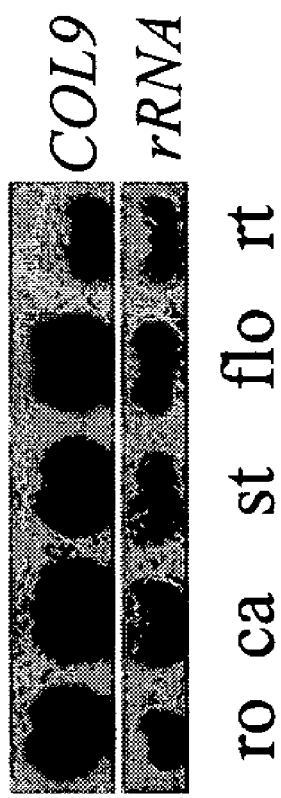
FIG. 3. COL9 mRNA abundance in different organs of wild-type plants, samples were collected after 12 h of light. ro: rosette leave; ca: cauline leave; st: stem; flo: flower; rt: root.

The spatial expression pattern of COL9 was examined at 12 hours after dawn in LD conditions. Northern hybridization analysis revealed the presence of the COL9 transcript in all sampled tissues: rosette leaf, cauline leaf, stem, flower and root (FIG. 3). The transcript level was relatively low in root (FIG. 3).

Figure 4:
FIG. 4. GUS staining of transgenic plants carrying GUS gene under the control of COL9 promoter at various development stages and in different organs: (A) 4 d old seedling; (B) 6 d old seedling; (C) 10 d old seedling; (D) 20 d old plant; (E) mature plant before bolting; (F) shoot apex and young flower bud; (G) inflorescence; (H) root; (I) flower; (J-L) silique.

Transgenic plants were further generated using the COL9 promoter driven GUS construct to examine reporter gene expression throughout the developmental stages. The expression of GUS was first detected in cotyledon, but not detectable in hypocotyl and root in 4 day old seedlings (FIG. 4A). Later on, GUS was present at the joint region of hypocotyl and root. In 6 day old seedlings, GUS was detected in cotyledon, leaf and hypocotyl with highest expression observed in vascular tissues (FIG. 4B). At the later stage of vegetative growth, GUS was continuously detected in rosette leaf and root, with strong staining in vascular tissues, and weak staining at shoot apex (FIGS. 4C-E). GUS staining was also observed in root including root cap, but staining was not seen in the division zone of root (FIG. 4H). At the reproductive stage, GUS staining was also detected in rosette leaf, cauline leaf and stem (FIGS. 4F, G). Young flower buds showed low levels of GUS staining (FIG. 4F, G). Later, GUS was detected in the vascular tissues of petal, sepal and filament, but not in anther and stigmas (FIG. 4I). Low expression of GUS was detected in young silique, increased in old silique, and not detectable in seeds (FIG. 4J-L). Thus, when the GUS gene was under the control of the COL9 promoter, high levels of expression was found in different organs throughout plant development.

Example 3

Overexpression of COL9 Delays Flowering Time Under Long Day Conditions

To understand the function of COL9, transgenic plants carrying a sense COL9 gene under the control of a CaMV35S promoter were generated and analyzed under long day and short day conditions. Twenty two kanamycin resistant plants were sampled for northern hybridization analysis. Nine plants showed high expression levels of exogenous COL9 transcript due to overexpression of the transgene (FIG. 5A) and 13 plants displayed low expression levels of both the exogenous and the endogenous transcripts (FIG. 5A), which was apparently caused by cosuppression of the introduced COL9 with the endogenous COL9.

Figure 5:
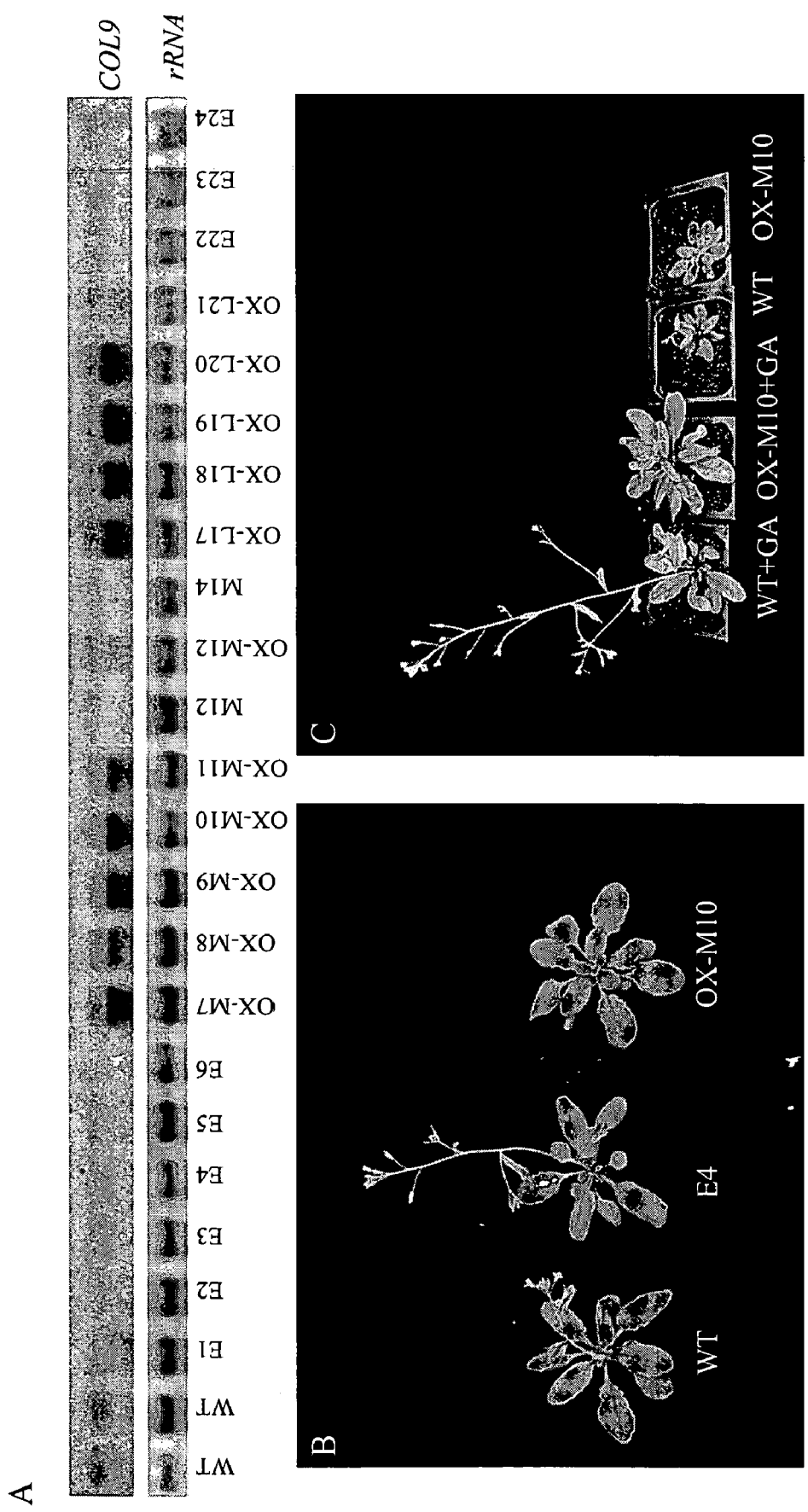
FIG. 5. Transcript accumulation and phenotype of COL9 transgenic plants. (A) Northern blot hybridization analysis of plants transformed with 35S::COL9. (B) Phenotypes of transgenic plants under long-day conditions, WT: wild-type; E4: COL9 cosuppression line, early flowering; OX-M10: COL9 overexpression line, late flowering. (C) Effect of gibberellin spray on flowering time of wild-type and overexpression line OX-M10 under long-day conditions.

To test the effect of COL9 up-regulation or down-regulation on flowering time, three highly over-expressed lines designated OX-M10, OX-L18 and OX-L19, and three strongly co-suppressed lines designated E4, E23 and E24, were used for the determination of flowering time. Bolting date was observed, and total leave number (TLN), including rosette leaves and cauline leaves on primary stem was recorded as a measurement of flowering time. Under long day conditions, the appearance of flower buds in COL9 overexpression lines was 5-7 days later than wild type plants, whereas the cosuppression lines had visible flower buds 1-2 days earlier than wild type plants (FIG. 5B). Table 1 shows that the overexpression lines produced significantly more leaves than wild type plants, and the cosuppression lines had slightly less number of leaves than wild type plants.

When transgenic plants were grown under short day conditions, both overexpression lines and cosuppression lines flowered at almost the same time and generated similar number of leaves compared to wild type plants. Therefore, up-regulation of COL9 significantly delayed flowering and down-regulation of COL9 slightly promoted flowering under long day conditions. The change of COL9 expression level had no significant impact on the flowering time under short day conditions. The results indicate that COL9 functions as a repressor in the photoperiodic pathway.

To further confirm the effects of down-regulation of COL9 on flowering time, a T-DNA insertion line, SALK137167, was obtained from the Ohio State *Arabidopsis* Biological Resource Center (ARBC). The location of the T-DNA insertion was confirmed by PCR and sequencing in the first exon of COL9, and northern analysis showed the disruption of COL9 transcripts. Like the COL9 cosuppression lines, the T-DNA insertion line flowered slightly earlier than wild type plants under long day conditions (Table 1).

TABLE 1

Effect of COL9 misexpression on flowering time of *Arabidopsis* under long-day conditions

| Genotype | Rosette leaves | Cauline leaves | Total leaf number |
| --- | --- | --- | --- |
| Columbia wild type | 11.95 ± 1.12 | 2.60 ± 0.66 | 14.55 ± 1.53 |
| OX-M10* | 16.65 ± 1.66 | 3.87 ± 0.74 | 20.52 ± 2.40 |
| OX-L18* | 16.18 ± 1.56 | 3.59 ± 0.58 | 19.77 ± 2.13 |
| OX-L19* | 16.08 ± 1.53 | 3.62 ± 0.47 | 19.77 ± 1.90 |
| E4** | 9.65 ± 0.85 | 2.30 ± 0.56 | 11.95 ± 1.41 |
| E22** | 10.89 ± 0.81 | 2.50 ± 0.50 | 13.39 ± 1.01 |
| E24** | 11.00 ± 1.14 | 2.69 ± 0.38 | 13.68 ± 1.24 |
| col9-T*** | 10.31 ± 0.96 | 2.31 ± 0.58 | 12.62 ± 1.39 |

*COL9 overexpression transgenic lines
**COL9 cosuppression transgenic lines
***COL9 T-DNA insertion line (Salk137167)

Figure 6:
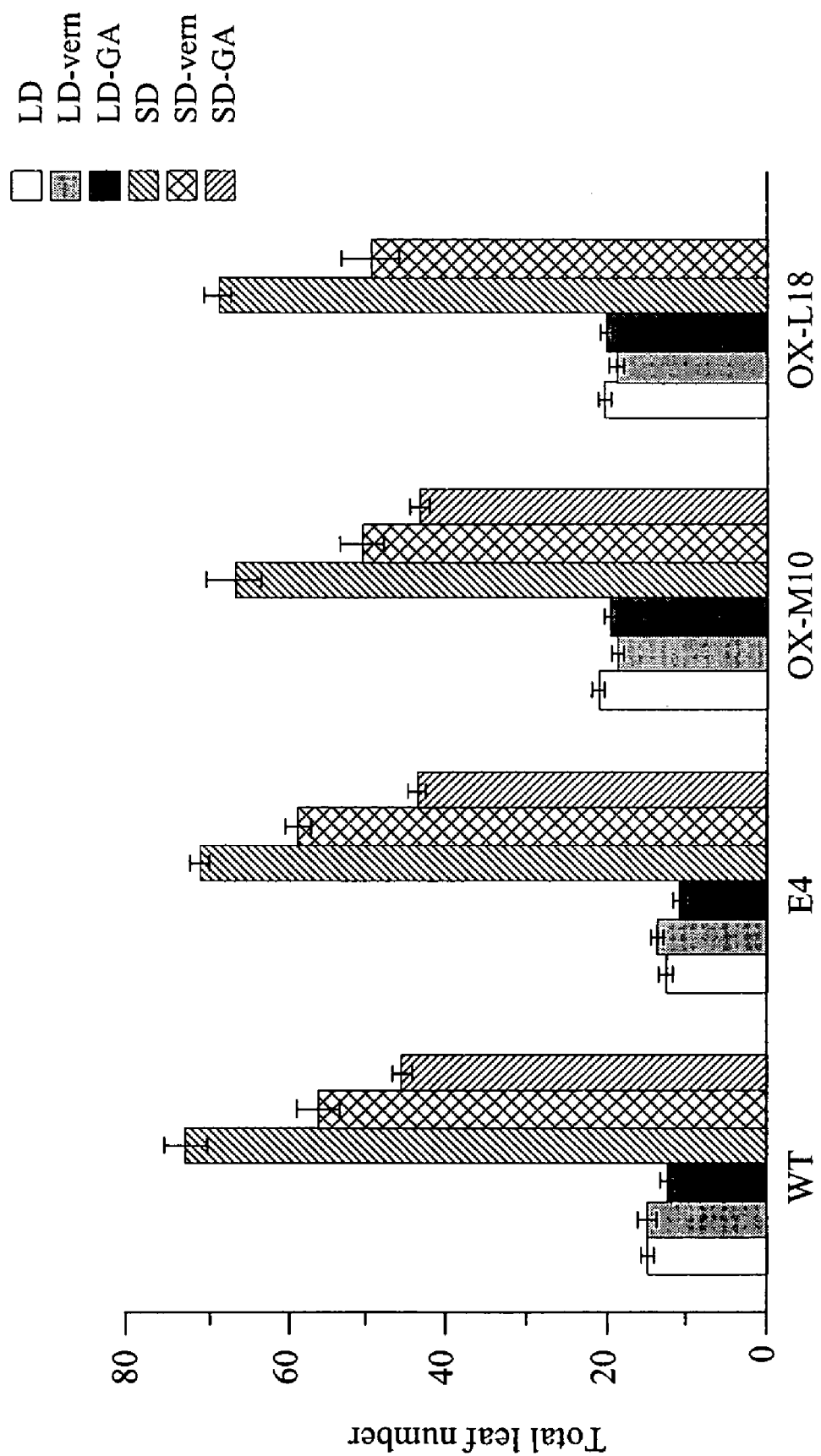
FIG. 6. Effects of COL9 transgene on flowering time under LD (16 h light/8 h dark), SD (8 h light/16 h dark), gibberellin spray (100 μm, twice a week) and vernalization treatment (6° C., 4 wk). E4: cosuppression line; OX-M10 and OX-L18: overexpression lines.

To determine if COL9 is involved in other flowering time control pathways, the effects of gibberellin (GA3) spray and vernalization treatments were analyzed with respect to flowering time of COL9 transgenic lines. Similar to wild type plants, flowering time of the transgenic lines was accelerated by both vernalization and gibberellin treatment (FIG. 5C, FIG. 6). Under long day conditions, the bolting time of the overexpression lines was still about 5 days later on average, and the total leaf number was significantly more than wild type plants after vernalization and gibberellin treatments. The cosuppression lines still flowered slightly earlier than wild type plants (FIG. 6). Under short day conditions, the overexpression lines and the cosuppression line did not show significant differences in flowering time when compared with wild type plants (FIG. 6). The results indicate that both the application of GA3 and vernalization could not complement the disruption of flowering time in COL9 transgenic lines.

Example 4

Overexpression of COL9 Delays Flowering by the Repression of CO as Well as FT

Figure 7:
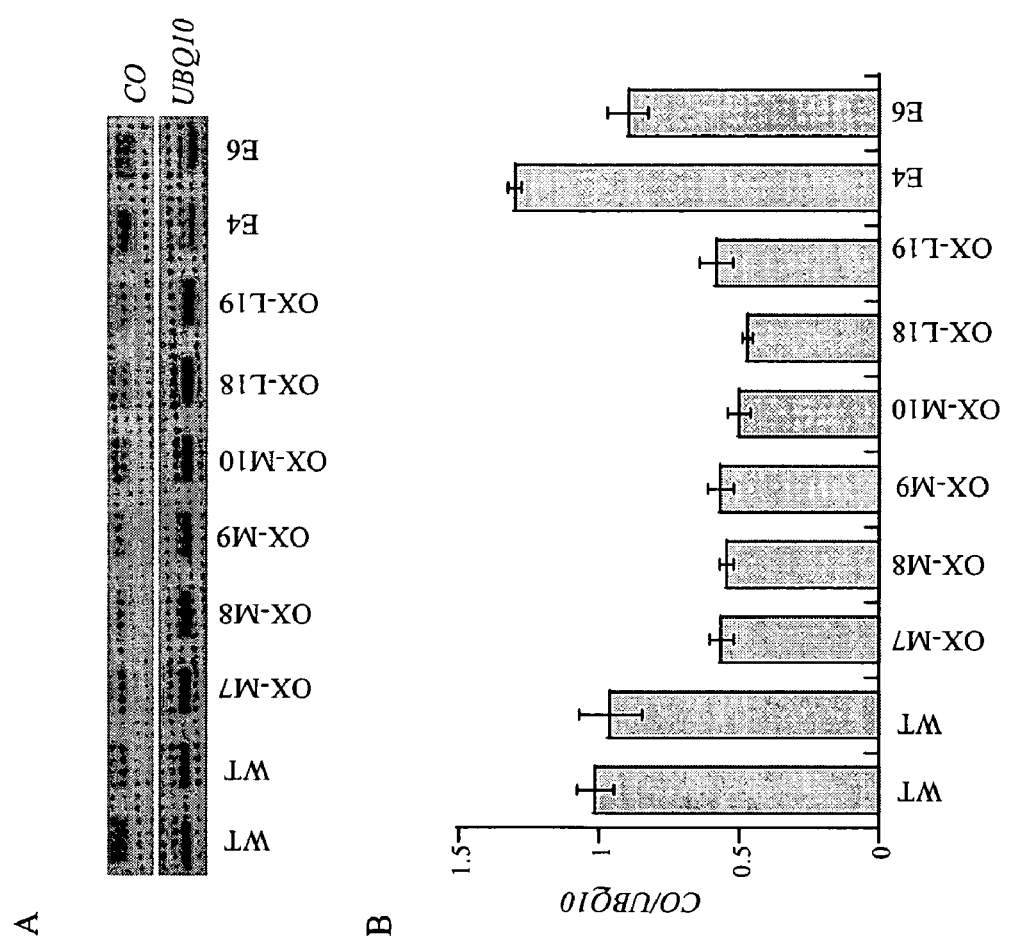
FIG. 7. Expression of CO in COL9 overexpression and cosuppression lines. (A) CO expression at 12 h after dawn in 35S::COL9 transgenic lines under long-day conditions. RT-PCR was used to detect CO (31 cycles) and UBQ10 (24 cycles). E4, and E6 are cosuppression lines; OX-M7-OX-M10, OX-L18, OX-L19 are overexpression lines. (B) Quantification of CO expression from the results in (A).
Figure 8:
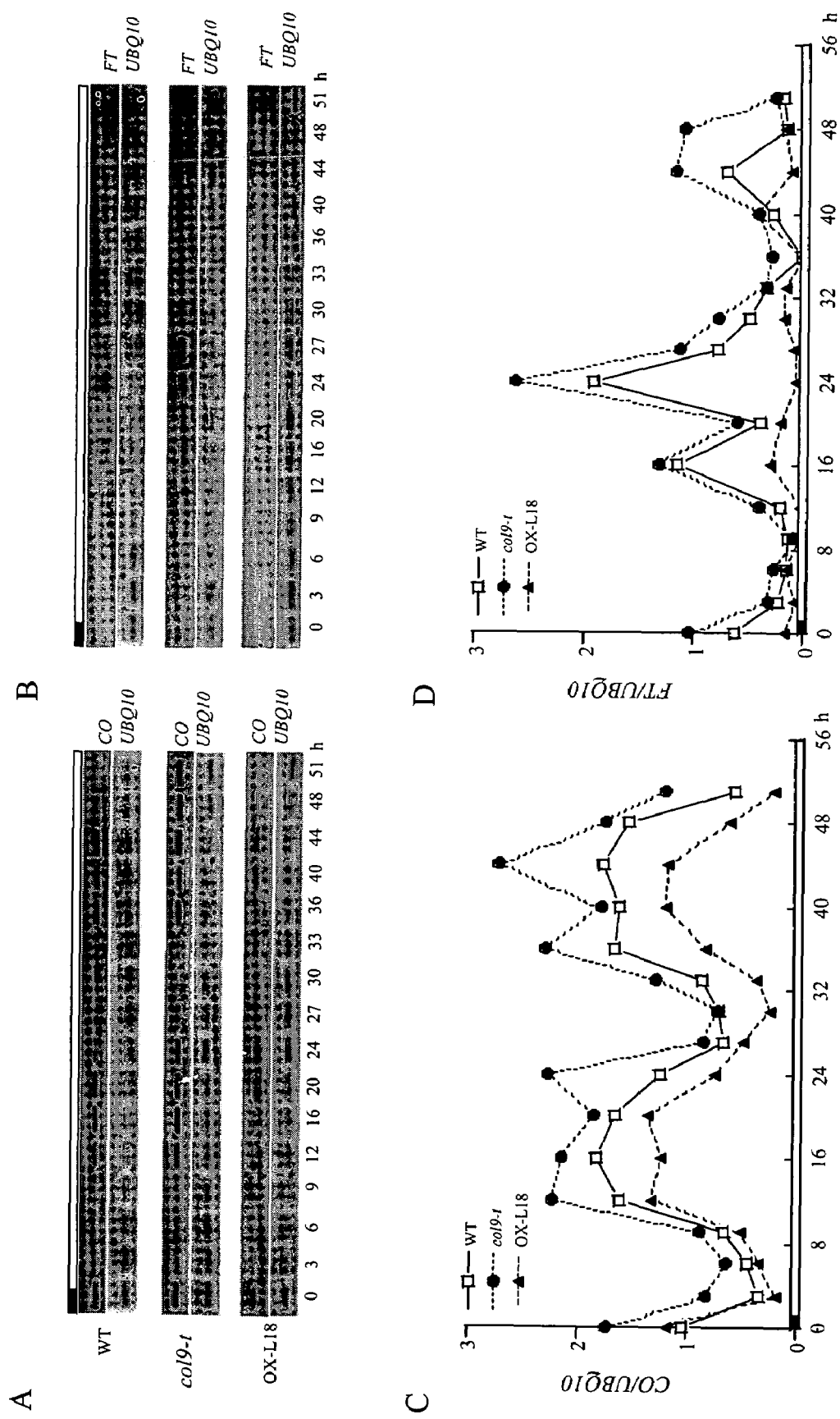
FIG. 8. Expression of CO and FT in COL9 transgenic lines under continuous light conditions. (A) RT-PCR detection of CO (31 cycles), FT (25 cycles) and UBQ10 (24 cycles) in wild-type plants (WT), COL9 T-DNA insertion line (col9-t), and COL9 overexpression line (OX-L18). (B) Quantification of CO expression from the results in (A). (C) Quantification of FT expression from the results in (A).

The above analysis of the transgenic lines showed that the influence of COL9 on flowering time is day-length dependent. As CO is the last output in the photoperiod pathway, and co mutants cause late flowering in long day, it was tested whether the delay of flowering in COL9 overexpression lines was caused by the repression of CO expression. A reduction of CO transcript abundance was consistently found in COL9 overexpression lines (FIGS. 7A, B). For detailed analysis, the oscillation of CO expression was compared at different time points under long-day and continuous light conditions (LL) in the transgenic lines and wild type plants. Under LL, although CO expression waveforms were largely similar to the wild-type, the level of CO transcript in the overexpression line OX-L18 was reduced at all the timepoints, while the CO expression level in the T-DNA insertion line col9-t was enhanced (FIG. 8A, C). Under LD, the expression of CO in the COL9 overexpression lines was also reduced at different timepoints.

Since FT is an important floral integrator and a direct target of CO (Kardailsky et al., 1999; Kobayashi et al., 1999; Samach et al., 2000), the expression of FT was analyzed in the transgenic lines. Under LL, the oscillation pattern of the FT transcript showed two peaks at 16 h and 24 h (FIG. 8B, D). The peak levels of FT were much lower in the overexpression line OX-L18, whereas the expression levels of FT were higher in the T-DNA insertion line col9-t (FIG. 8B, D). Under LD, FT mRNA abundance showed a similar oscillation pattern with an expression peak at 16 h in both wild type and transgenic lines. Again, the peak levels of FT mRNA were much lower in the overexpression lines than in the wild-type.

Figure 9:
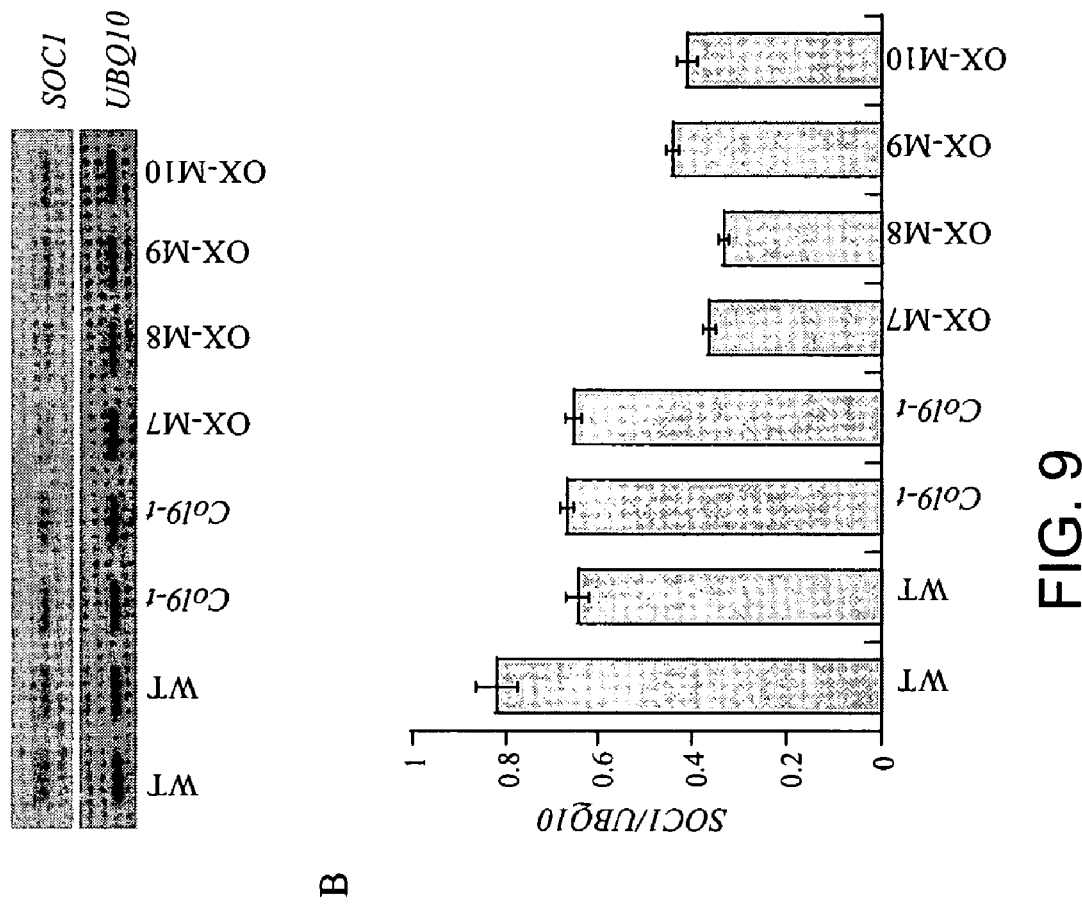
FIG. 9. Expression of SOC1 in COL9 transgenic lines under long-day conditions. (A) Expression of SOC1 in COL9 T-DNA insertion line (col9-t) and overexpression lines (OX-M7-10) at 12 h after dawn, SOC1 was detected by 28 cycles of RT-PCR. (B) Quantification of SOC1 expression from the results in (A).

The expression of the floral integrator SOC1, the other target of CO, was also analyzed in the transgenic plants. Like FT, the transcript level of SOC1 was reduced in COL9 overexpression lines (FIG. 9A, B).

Figure 10:
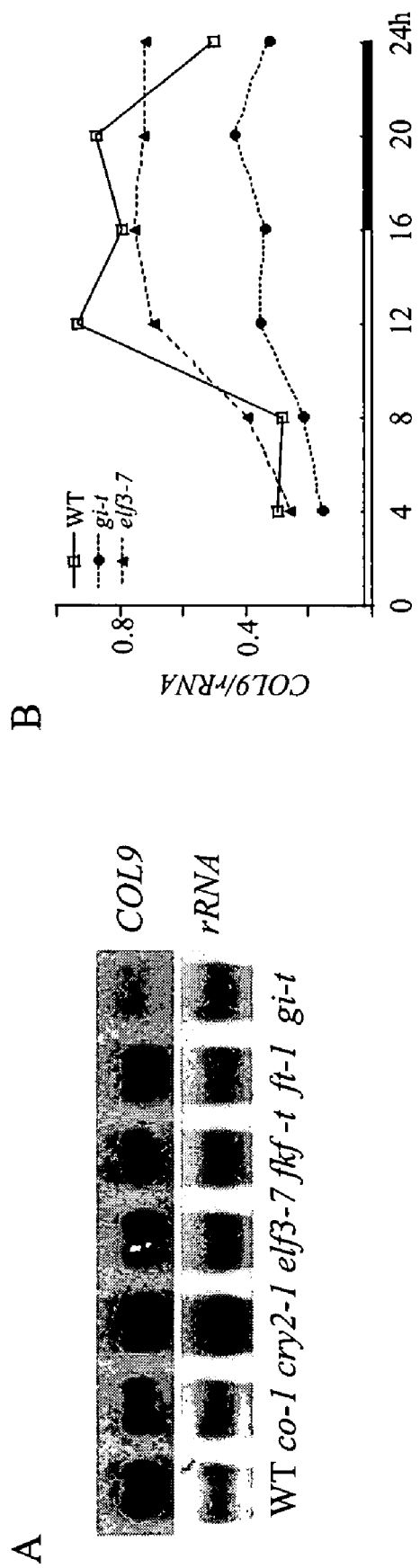
FIG. 10. Detection of COL9 expression in mutant lines by northern hybridization analysis. (A) COL9 mRNA accumulation at 12 h after dawn in mutants or T-DNA insertion lines. (B) COL9 oscillation patterns in WT, elf3-7 and gi-t under LD. Mutants: co-1, cry2-1, elf3-7 and ft-1; T-DNA insertion lines: fkf-T and gi-T; WT: wild-type.

In an effort to determine the potential upstream regulators of COL9, COL9 mRNA abundance was further analyzed at 12 h after dawn in several known photoperiod pathway mutants co-1, ft-1, elf3 (early flowering 3), cry2-1, and T-DNA insertion lines of GI (GIGANTEA) and FKF1 (FLA-VIN-BINDING, KELCH REPEAT, F-BOX). Northern hybridization analysis revealed a reduction of COL9 transcript level in the GI T-DNA insertion line, whilst no significant alteration of the mRNA abundance was found in the other tested lines (FIG. 10A). Further oscillation pattern analysis confirmed that the levels of COL9 transcript were consistently reduced at different timepoints in gi-t (FIG. 10B). Taken together, the results indicate that COL9 functions downstream of the circadian clock and is affected by GI.

Example 5

Figure 11:
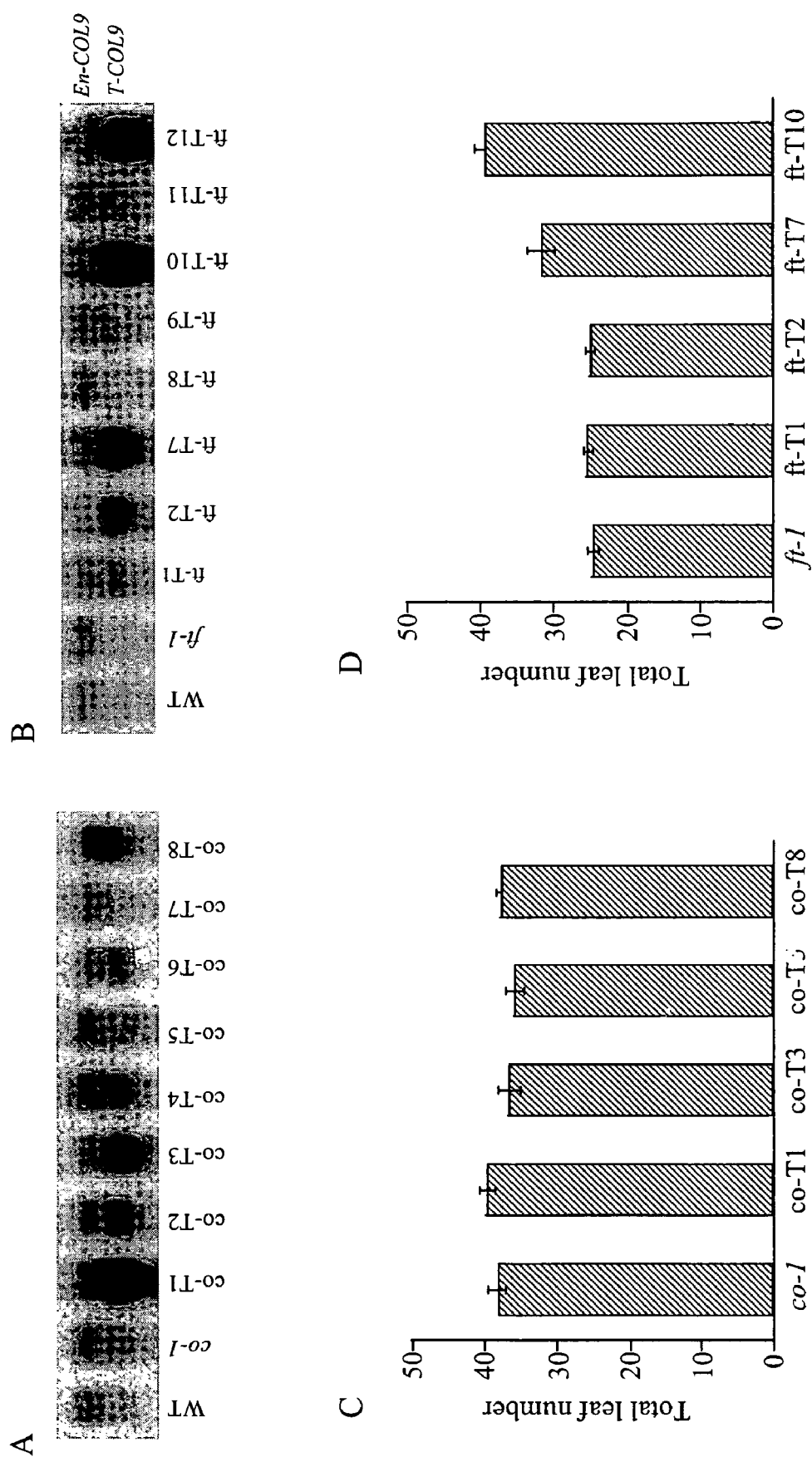
FIG. 11. Northern hybridization and flowering time of COL9 transgenic lines in ft-1 and co-1 backgrounds. (A) COL9 mRNA accumulation of 35S::COL9 transgenic lines in co-1 background. (B) COL9 mRNA accumulation in 35S::COL9 transgenic lines in ft-1 background. (C) Flowering time of COL9 transgenic lines in co-1 background (co-T1, co-T3, co-T5, and co-T8). (D) Flowering time of COL9 transgenic lines in ft-1 background (ft-T1, ft-T2 ft-T7 and ft-T10). En-COL9: endogenous expression; T-COL9: COL9 transgene expression.

Overexpression of COL9 Does not Enhance the Late Flowering Phenotype of co-1 Mutants A 35S::COL9 gene construct was introduced into co-1 and ft-1 mutant background. Transgenic lines with various expression levels of the transgene were used to investigate the effect of COL9 overexpression on flowering time. In a co-1 background, COL9 overexpression lines (co-T1, co-T3, co-T5 and co-T8) showed similar flowering time to co-1 mutant, even for the line co-T8, which showed a very high level of COL9 expression (FIG. 11A, C). Thus, overexpression of COL9 did not further delay flowering in co-1 mutant.

In an ft-1 background, two transgenic lines ft-t1 and ft-t2, which overexpressed COL9 at relatively low levels, flowered at similar time to ft-1 mutant (FIG. 11B, D). Line ft-t7 had an intermediate level of COL9 expression, its average leaf number was more than ft-1. The highest COL9 overexpressor, ft-t10, flowered significantly later than the ft-1 mutant (FIG. 11B, D). The results showed that high levels of COL9 overexpression could enhance the late flowering phenotype of ft-1, but even so, the transgenic line did not flower significantly later than the co-1 mutant.

Example 6

COL9 Functions as a Negative Regulator of Flowering in the Photoperiodic Pathway The photoperiod pathway mediates light and temporal signals into flowering time regulation and promotes flowering under LD conditions. The abundance of COL9 transcript displayed a diurnal rhythm under different light conditions, indicating COL9 is a circadian regulated gene. It is known that the circadian clock regulates the expression of genes that act in the LD pathway, and the circadian clock itself entrained (or synchronized) to the daily cycle of light and dark (Reeves and Coupland, 2000). CCA1, LHY and TOC1 may be part of the central mechanism that generates circadian rhythms in plants (Searle and Coupland, 2004). CCA1 and LHY are similar in sequence and expression and are genetically partially redundant (Mizoguchi et al., 2002; Wang and Tobin, 1998). Circadian clock and flowering time is also affected by other genes such as ELF3 and FKF1. EFL3 may function in the circadian clock input pathway; mutation of ELF3 results in early flowering and disrupts circadian regulation in LL (Hicks et al., 2001; McWatters et al., 2000). FKF1 is a potential blue photoreceptor involved in photoperiod-specific light signaling (Imazumi et al., 2003); deletion of FKF1 delays flowering and alters expression patterns of CCA1 and CAB1 (Nelson et al., 2000). The alteration of COL9 expression did not influence the expression pattern and amplitude of clock genes CCA1 and TOC1, and the clock regulated output CCR2. In addition, the expression of exogenous COL9 has no effect on the regulation of endogenous COL9 expression. Therefore, COL9 is not involved in the regulation of circadian clock but rather acts at downstream of the clock.

GI is implicated in the control of flowering in response to daylength. GI mRNA expression exhibits a circadian rhythm and gi mutations cause delayed flowering and exhibit defects in clock function (Fowler et al., 1999; Koornneef et al., 1991; Park et al., 1999). The amplitude of CO mRNA expression is reduced in gi mutants (Suárez-López et al., 2001), indicating that GI acts upstream of CO (Simpson, 2003). Because the major effect of gi mutations on flowering appears to be through the regulation of CO mRNA levels, recent work has put GI in the pathway between the circadian clock and CO (Hayama et al., 2003; Simpson, 2003; Searle and Coupland, 2004). Similar to CO, the expression level of COL9 is reduced in a gi mutant, suggesting that COL9 also acts downstream of GI. It seems that a balanced regulation of CO expression will finally determine the flowering time of gi mutants. Because the gi mutation also disrupts PHYB signaling and alters circadian rhythms (Huq et al., 2000; Park et al., 1999), it is not clear how the proposed hierarchy of GI and CO/COL9 relates to the role of GI in light signal transductio or in regulating circadian clock period length.

Down-regulation and T-DNA insertion of COL9 resulted in early flowering and fewer leaves, however, the phenotypic change was relatively small compared with its effect on delay flowering in the overexpression lines. Because another members of the CO family (COL10) also delays flowering when overexpressed (Example 8), we speculate that COL9 may share function redundancy with other gene(s) in floral regulation.

Although COL9 and CO belong to the same gene family, overexpression of COL9 delays flowering under LD conditions, which is opposite to the promotion role CO plays when overexpressed. Under SD conditions, the flowering time of both COL9 overexpression and cosuppression lines is similar to that of wild-type plants, indicating that COL9 is involved in flowering time regulation in a day-length dependent manner. GA3 spray and vernalization treatment did not affect flowering time of COL9 transgenic lines. Therefore, COL9 functions as a negative regulator of flowering in the photoperiod pathway.

Example 7

COL9 Regulates Flowering Time by Repressing the Expression of CO and Concomitantly Reducing the Expression of FT CO has been well documented to play a central role in the induction of flowering by LD in *Arabidopsis* (Putterill et al., 1995; Samach et al., 2000; Suárez-López et al., 2001; Hepworth et al., 2002; Valverde et al., 2004). However, little information has been available regarding the function of other CO family members. The only report on transgenic expression of other CO family members, COL1 and COL2, showed that they had little effect on flowering in *Arabidopsis* (Ledger et al., 2001). The studies here show for the first time that another CO family member, COL9, when overexpressed, reduces the expression of CO and delays flowering in LD, whereas down-regulation of COL9 increased CO mRNA abundance and promoted flowering in LD, indicating that the effect of COL9 on flowering time was through the negative regulation of CO. It is known that loss of function co mutants flower late in inductive LDs but like wild-type in SD (Putterill et al., 1995), this is consistent with the results herein showing that COL9 overexpression lines flower at the similar time as wild-type plants in SD. Furthermore, both COL9 and CO are functioning downstream of GI in the photoperiod pathway, and the overexpression of COL9 in co-1 mutant background did not enhance the late flowering phenotype of the mutant.

FT is an integrator of the flowering control network and a direct target of CO (Samach et al., 2000). Overexpression of CO activates the expression of FT, which promote flowering and whose expression is activated only under LD (Samach et al., 2000). In loss of function co mutants, FT expression was reduced (Kardailsky et al., 1999; Kobayashi et al., 1999). Although SOC1 is another target of CO, no consistent difference in SOC1 mRNA abundance was detected in comparisons of co mutant and wild-type seedlings (Samach et al., 2000). In the COL9 overexpression lines produced, the expression of FT is reduced when CO expression is repressed, while no consistent difference was found regarding the level of SOC1 expression. Thus it can be easily explained that due to the reduction of CO in the COL9 expressing lines, the expression of FT was reduced and flowering of plants was delayed. Further evidence supporting this explanation is the overexpression of COL9 in ft-1 mutant background, in which high expressors showed more severe flowering phenotype than ft-1, but the flowering time of the high expressors was no later than the co mutant.

A simplified summary of photoperiod response of flowering can be described based on the studies carried out: a linear pathway established through the action of photoreceptors that entrains the circadian clock, the function of which GI affects, which controls the expression of CO, which in turn activates the floral pathway integrator, FT, which promote the floral transition (Simpson, 2003). The question of how CO is activated under LD to bring about the expression of FT has been a key to understand the regulation of flowering time in *Arabidopsis* (Hayama and Coupland, 2003). A coincidence model for CO activation by photoreceptors has been proposed based on the striking temporal pattern of CO expression (Searle and Coupland, 2004). Under SD conditions, CO mRNA expression peaks during the night, and the downstream gene FT is not expressed, whereas under LD conditions, the peak of CO mRNA partly coincides with light, and the expression of FT mRNA is activated (Suárez-López et al., 2001; Searle and Coupland, 2004). The model proposes that CO is responsible for determining the light sensitive phase through its diurnal expression pattern: if plants are exposed to light at a time when CO expression is high, flowering is promoted through the activation of CO (Hayama and Coupland, 2003). It is interesting to note that there is also a coincidence between the expression patterns of COL9 and CO: Under SD conditions, high level COL9 mRNA peaks immediately after dark, ahead of the CO peak, whereas under LD conditions, a relatively low level COL9 mRNA peaks at night, which is after the CO peak. Because COL9 plays an antagonistic role to CO, the coincidence of COL9 and CO mRNA accumulation offers another explanation on the regulation of CO in the photoperiod pathway: COL9 represses CO expression in SD, but the repression effect is relieved under LD.

Example 8

Figure 12:
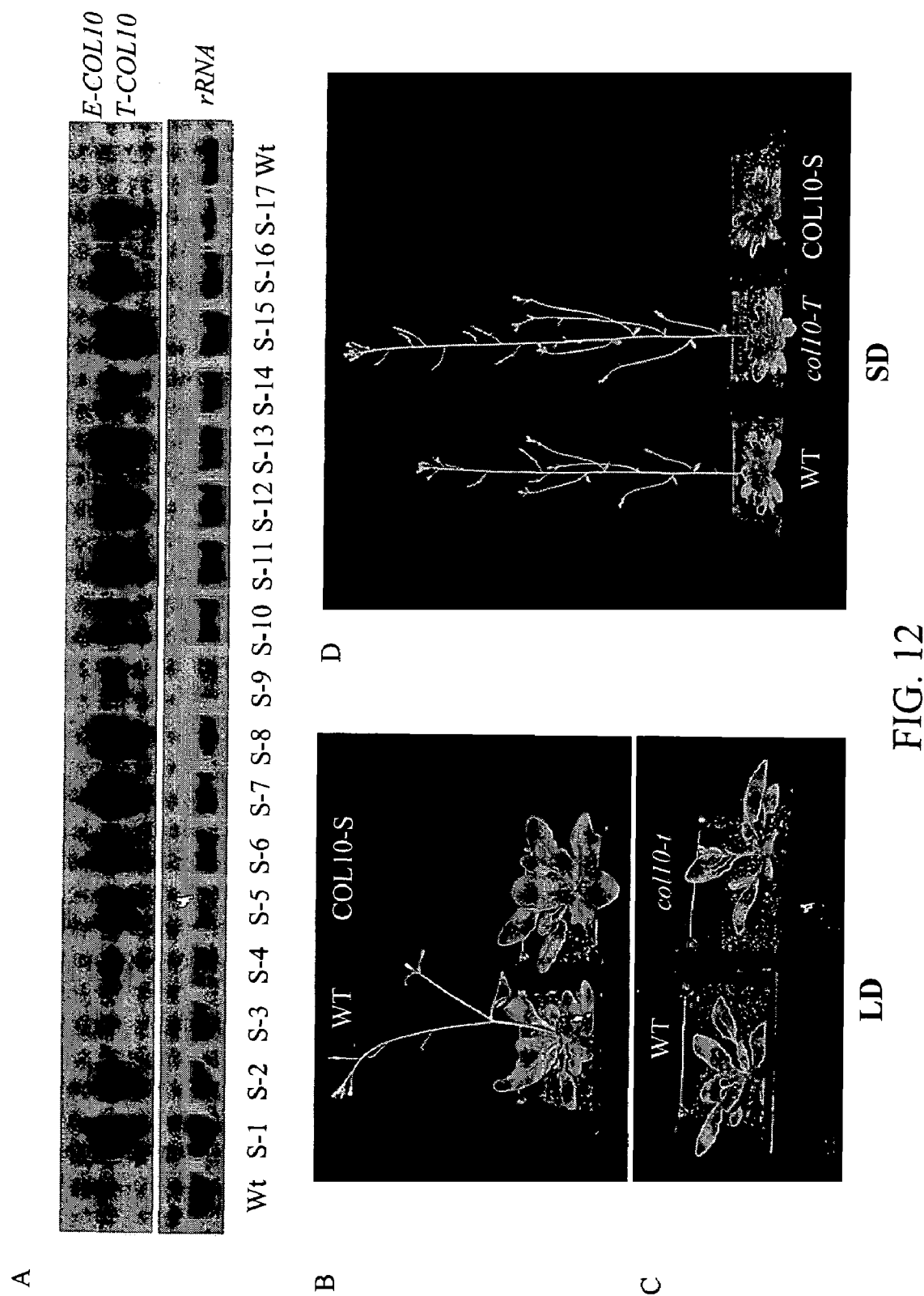
FIG. 12. Transcript accumulation and phenotype of COL10 transgenic Arabidopsis plants. (A) Northern blot hybridization analysis of plants transformed with 35S::COL10. S1-17: COL10 transgenic plants. (B, C) Phenotype of transgenic plants under long day conditions. (D) Phenotype of transgenic plants under short-day conditions. WT: wild-type; COL10-S: COL10 overexpression line, late flowering: col10-t: COL10 T-DNA insertion line.
Figure 13:
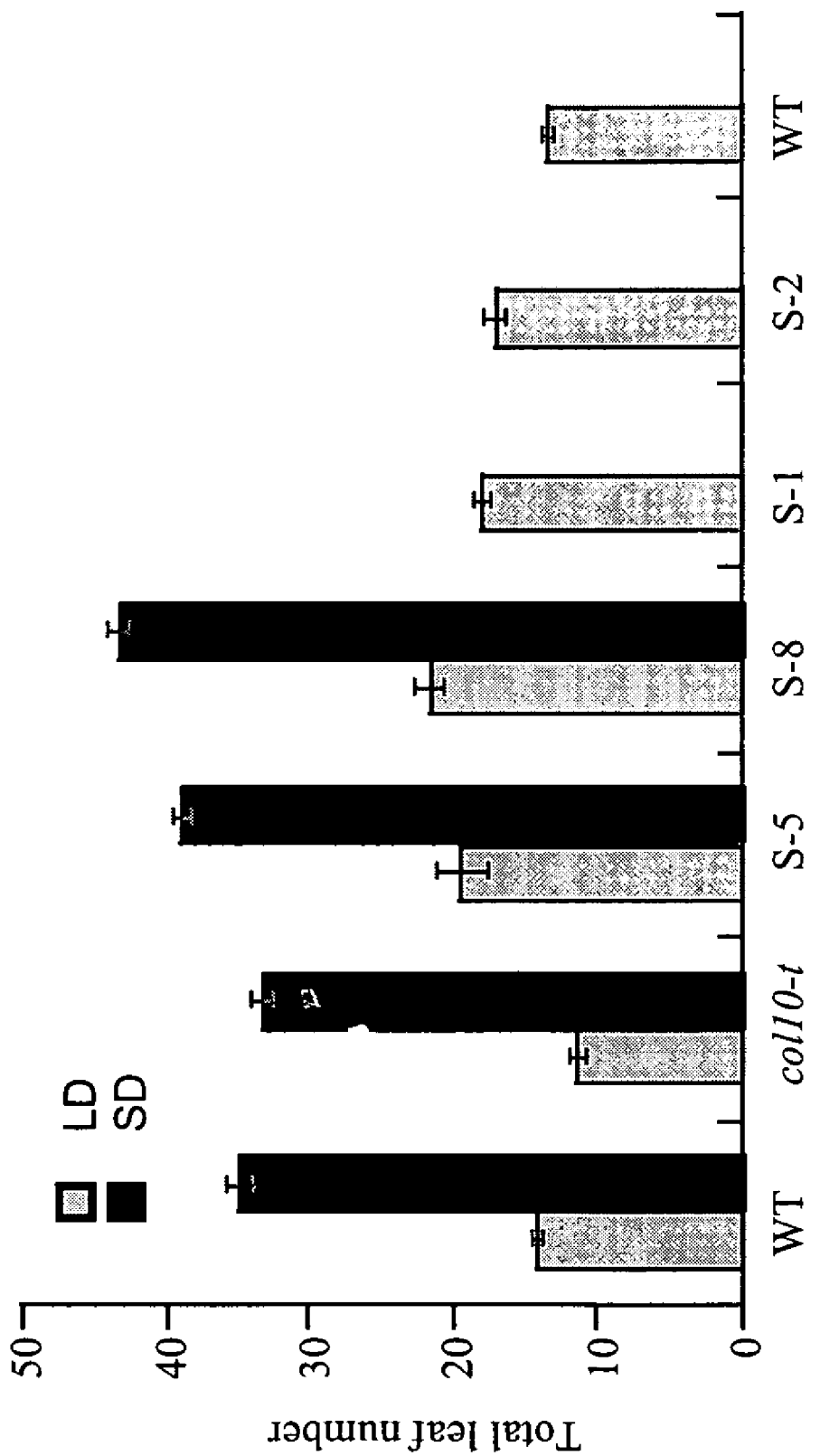
FIG. 13. effects of COL10 transgene on flowering time under LD (16 h light/8 h dark). SD (8 h light/16 h dark). WT: wild-type; S1, S2, S5, and S8: COL10 overexpression lines; col10-t COL10 T-DNA insertion line.

Overexpression of COL10 Delays Flowering Time Under Both Long-Day and Short-Day Conditions COL10 (SEQ ID NO:35) is another member of the CO family, it shares 70.2% identity to COL9. To understand the function of COL10, transgenic plants carrying a sense COL10 transgene (SEQ ID NO:34) under the control of a CaMV35S promoter were generated and analyzed. Seventeen hygromycin resistant plants were sampled for northern hybridization analysis, sixteen plants expressed transgenic COL10 (FIG. 12A). To test the effect of COL10 up-regulation on flowering time, four highly over-expressed lines designated S-1, S-2, S-5 and S-8 were grew under long-day and short-day conditions to observe flowering time as above. Under both long-day and short day conditions, COL10 transgenic plants showed late flowering compared to wild-type plants (FIG. 12B, C, D), and more leaves produced on primary stems of the transgenics (FIG. 13).

Furthermore, a T-DNA insertion line, SALK061961, was obtained from the Ohio State *Arabidopsis* Biological Resource Center (ARBC). The location of the T-DNA insertion was confirmed by PCR and sequencing in the last exon of COL10, and northern analysis showed a larger size of COL10 transcript. Opposite to the phenotype of COL10 overexpression plants, the T-DNA insertion line (col10-t) showed slightly early flowering under long-day and short-day conditions (FIG. 12C-D; FIG. 13).

Example 9

Materials and Methods

A. Plant Material and Growth Conditions

*Arabidopsis thaliana* ecotype Columbia was used in the experiments. COL9 (col9-T, SALK137167), GI (gi-t, SALK092757) and FKF (fkf-t, SALK059480) T-DNA insertion lines and co-1 (CS3122), ft-1 (CS56) and cry-2 (CS3732) mutants were obtained from ABRC. Gene constructs and the generation of COL9 and COL10 transgenic plants are described below. T3 homozygous COL9 overexpression lines OX-M10 and OX-L18 and the cosuppression line E4 were analyzed in detail.

Seeds were surface sterilized with bleach and sowed on MS (Murashige and Skoog, 1962) agar medium containing 2% Sucrose. After stored in darkness at 4° C. for 2 days, seeds were germinated for 10 d and seedlings were transferred to soil and grown in growth chamber (23° C. day/19° C. night).

For circadian rhythm analysis, three photoperiod conditions were used in similar growth chambers: short day (SD), 8 hours light and 16 hours darkness; long day (LD), 16 hours light and 8 hours darkness; continuous long day (LL), normal short day followed by continuous light. A combination of fluorescent tubes and incandescent bulbs was used. Light intensity was ~220-240 µmol $m^{-2}$ $s^{-1}$.

For vernalization treatment, seeds were sowed on the MS medium and stored at 6° C. for 4 weeks, and then the seedlings were planted into soil in growth chamber under SD or LD conditions. For gibberellins treatment, 10-12 days old seedlings were transplanted into pots and sprayed with 100 µm gibberellins twice a week in LD and SD growth room.

B. Gene Expression Analysis

Northern hybridization: For circadian rhythm analysis, leaves from 4 weeks old wild-type plants were collected in 4 hour internal for 48 hours in SD, LD and LL conditions. Each sample was collected from 2 plants. For gene expression analysis, the samples were collected at 12 hours after light entrance, when COL9 and COL10 show high mRNA abundance. Total RNA was isolated using TRI reagent (Molecular Research Center, Inc. #TR118-L) and RNA gel blotting was carried out according to standard protocols (Sambrook et al, 1989). The coding region of COL9 or COL10 was used as probe for the analysis of COL9 or COL10 expression, and a GUS fragment from pCAMBIA3301 vector was used for the analysis of GUS expression, Northern hybridizations were performed using the [$^{32}$P] dCTP-labeled probes following the QuikHyb® Hybridization protocols.

Semi-quantitative RT-PCR: For first strand cDNA synthesis, 2 µg total RNA for each sample was reverse-transcribed by using random primers in 20 µl reaction volume. Thereafter, the cDNA were diluted into 50 µl with DDH$_2$O, and a 2 µl aliquot was analyzed for gene expression by different PCR parameters. Specific primers for different flowering time genes were designed by DNAstar software to avoid detecting homologous genes. Primer sequences were: CO, forward-TCACCACCAAAGCGAGAAAA (SEQ ID NO:3), reverse-TGGCTTGCAGGGTCAGGTTG (SEQ ID NO:4); LFY: forward-GCGGCGAAGATAGCGGAGTTAGGT (SEQ ID NO:5), reverse-GTTGCCGTTATCCATCCCGTCGTC (SEQ ID NO:6); FLC: forward-TTCTCCAAACGTCG-CAACGGTCT (SEQ ID NO:7), reverse-GATTTGTCCAG-CAGGTGACATCTC (SEQ ID NO:8); FT, forward-TAG- TAAGCAGAGTTGTTGGAGACG (SEQ ID NO:9), reverse-GGGAAGGCCGAGATTGTAGAT (SEQ ID NO:10); SOC1: forward-CTTTCTTTCTTCTTCTCCCTC-CAG (SEQ ID NO:11), reverse-TTGCTCGAATA-CATTTGACACTTT (SEQ ID NO:12); UBQ10, forward-GTGTTGCGTCTGCGTGGAGGTA (SEQ ID NO:13), reverse-TTGTCATTAGAAAGAAAGAGATA (SEQ ID NO:14); CCA1: forward-GCCGCAACTTTCGCCTCAT-CAT (SEQ ID NO:19), reverse-TGCATCCGCCTCAACAT-CATCAC (SEQ ID NO:20); CCR2: forward-AGTTGAG-TACCGGTGCTTTGTCG (SEQ ID NO:21), reverse-CCGCCTCCACCAGATCCGTAACCT (SEQ ID NO:22); PCR amplification products were analyzed by electrophoresis in 1% agarose/ethidium bromide gels. UBQ10 was used as standard for normalization.

C. Generation of Gene Constructs and Genetic Transformation

35S::COL9 sense construct: COL9(At3g07650) open reading frame was cloned by RT-PCR and ligated in sense orientation under the control of the cauliflower mosaic virus 35S promoter at XhoI and XbaI restriction sites in pRTL2 vector. Primer sequences: forward-TTCTCGAGATGGGT-TACATGTGT (SEQ ID NO:15), reverse-TGTCTAGAT-CAATAACTTCTGGTT (SEQ ID NO:16). The fragment 35S::COL9 was subcloned into the binary vector pCAMBIA 2300 at a HindIII restriction site.

COL9::GUS construct: A 1235 bp genomic sequence from the upstream of COL9 start codon was cloned as the COL9 promoter. Primer sequences: forward-CTCTAGAAAAAT-TAACACTTGCTCA (SEQ ID NO:17), reverse-ACCATG-GCCTTCTTGTGGACTACTACTAT (SEQ ID NO:18). The promoter was subcloned into the binary vector pCAMBIA 3301 at XbaI and NcoI restriction sites to replace the CaMV 35S promoter in front of the reporter gene GUS.

35S::GFP-COL9 construct: A pCAMBIA3300 vector carrying a Hind III-EcoR I fragment from the CaMV35S-sGFP (S65T)-nos plasmid (Chiu et al., 1996) was digested by Not I and BsrG I, and the COL9 ORF was inserted into the vector before the stop codon of sGFP and in frame with sGFP. The resulting 35S::sGFP-COL9 construct was delivered into onion epidermal cells by particle bombardment.

35S::COL10 sense construct: COL10 (At4g48250) open reading frame (SEQ ID NO:34) was cloned by RT-PCR and ligated in sense orientation under the control of the cauliflower mosaic virus 35S promoter at BglII and BstE II restriction sites in binary vector pCAMBIA 1305. Primer sequences: forward-GTAGATCTGATGGGTTATATGT-GTGA (SEQ ID NO:36); reverse-GGTCACCTCAGCTTCT-TGTTGGGCTCAT (SEQ ID NO:37).

Transformation: DNA of the binary vectors was transferred into the *Agrobacterium* strain C58 by the freeze-thaw method (Chen et al., 1994). Transgenic *Arabidopsis* plants were generated following the floral dip protocol method (Clough and Bent 1998).

D. Measurement of Flowering Time

Flowering time was measured as total leaf number (TLN) as described by Koornneef et al. (1991). The final number of rosette leaf and cauline leaf in the main inflorescence (not including leaves on axillary inflorescences) was counted on the day when the first petals became visible.

E. GUS Staining:

Three COL9::GUS transgenic lines were analyzed in detail. Samples were collected throughout the developmental stages, from the beginning of seed germination to seeds maturation, and stained in GUS staining solution (Spangenberg et al., 1995).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,468
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
Bates, *Mol. Biotechnol.*, 2(2):135-145, 1994.
Battraw and Hall, *Theor. App. Genet.*, 82(2):161-168, 1991.
Bevan et al., *Nucleic Acids Research*, 11(2):369-385, 1983.
Bhattachaijee; An; Gupta, *J. Plant Bioch. and Biotech.*, 6, (2):69-73. 1997.
Bouchez et al., *EMBO Journal*, 8(13):4197-4204, 1989.
Bower et al., *Plant Journal*, 2:409-416. 1992.
Buchanan-Wollaston et al., *Plant Cell Reports* 11:627-631. 1992
Buising and Benbow, *Mol Gen Genet*, 243(1):71-81. 1994.
Callis, Fromm, Walbot, *Genes Dev.*, 1:1183-1200, 1987.
Casa et al., *Proc. Natl. Acad. Sci. USA*, 90(23):11212-11216, 1993.
Chandler et al., *The Plant Cell*, 1:1175-1183, 1989.
Chen et al., *Biotechniques*, 16:664-670, 1994.
Chiu et al., *Curr. Biol.*, 6(3):325-330, 1996.
Christou; et al., *Proc. Natl. Acad. Sci. USA*, 84(12):3962-3966, 1987.
Chu et al., *Scientia Sinica*, 18:659-668, 1975.
Clough and Bent, *Plant Journal*, 16:735-743, 1998.
Conkling et al., *Plant Physiol.*, 93:1203-1211, 1990.
De Block et al., *EMBO Journal*, 6(9):2513-2518, 1987.
De Block, De Brouwer, Tenning, *Plant Physiol.*, 91:694-701, 1989.
Dellaporta et al., In: *Chromosome Structure and Function: Impact of New Concepts*, 18th Stadler Genetics Symposium, 11:263-282, 1988.
Denmark Patent DE 3642 829
D'Halluin et al., *Plant Cell*, 4(12):1495-1505, 1992.
Ebert et al., 84:5745-5749, *Proc. Natl. Acad. Sci. USA*, 1987.
Ellis et al., *EMBO Journal*, 6(11):3203-3208, 1987.
European Patent 154,204
Fowler et al. *EMBO J.* 18:4679-4688, 1999.

Fraley et al., *Bio/Technology*, 3:629-635, 1985.
Fromm et al., *Nature*, 319:791-793, 1986.
Gallie et al., *Plant Cell*, 1:301-311, 1989.
Gelvin et al., In: *Plant Molecular Biology Manual*, 1990.
Griffiths et al., *Plant Physiol.*, 131:1855-1867, 2003.
Hagio et al., *Plant Cell Rep.*, 10(5):260-264, 1991.
Hamilton et al., *Proc. Natl. Acad. Sci. USA*, 93(18):9975-9979, 1996.
Harmer et al., *Science*, 290:2110-2113, 2000.
Haseloff et al., *Proc. Natl. Acad. Sci. USA*, 94(6):2122-2127, 1997.
Hayama and Coupland, *Curr. Opin. Plant Biol.*, 6(1):13-19, 2003.
Hayama et al., *Nature*, 422(6933):719-722, 2003.
He et al., *Plant Cell Reports*, 14(2-3):192-196, 1994.
Hensgens et al., *Plant Mol. Biol.*, 22(6):1101-1127, 1993.
Hepworth et al., *EMBO J.*, 21(16):4327-4337, 2002.
Hiei et al., *Plant Mol. Biol.*, 35(1-2):205-218, 1997.
Hinchee et al., *Bio/Technol.*, 6:915-922, 1988.
Hou and Lin, *Plant Physiology*, 111:166, 1996.
Hudspeth and Grula, *Plant Mol. Biol.*, 12:579-589, 1989.
Huq et al., *Proc. Nat. Acad. Sci. USA*, 97:9789-9794, 2000.
Ikuta et al., *Bio/Technol.*, 8:241-242, 1990.
Imazumi et al., *Nature*, 426:302-306, 2003.
Ishida et al., *Nat. Biotechnol.*, 14:745-750, 1996.
Kaeppler et al., *Plant Cell Reports* 9: 415-418, 1990.
Kaeppler et al., *Theor. Appl. Genet.*, 84(5-6):560-566, 1992.
Kardailsky et al., *Science*, 286:1962-1965, 1999.
Katz et al., *J. Gen. Microbiol.*, 129:2703-2714, 1983.
Knittel et al., *Plant Cell Reports*, 14(2-3):81-86, 1994.
Kobayashi et al., *Science*, 286:1960-1962, 1999.
Koornneef et al., *Annu. Rev. Plant Physiol. Plant Mol. Biol.*, 49:345-370, 1998.
Koornneef et al., *Mol. Gen. Genet.*, 229:57-66, 1991.
Lawton et al., *Plant Mol. Biol.* 9:315-324, 1987.
Lazzeri, *Methods Mol. Biol.*, 49:95-106, 1995.
Ledger et al., *Plant Journal*, 26:15-22, 2001.
Lee et al., *Genes Dev.* 14:2366-2376, 2000.
Lee; Suh; Lee, *Korean J. Genet.*, 11(2):65-72, 1989.
Levy and Dean, *Plant Cell*, 10:1973-1989, 1998.
Lorz et al., *Mol Gen Genet*, 199:178-182, 1985.
Marcotte et al., *Nature*, 335:454, 1988.
McCabe and Martinell, *Bio-Technology*, 11(5):596-598, 1993.
McCormac et al., *Euphytica*, 99(1):17-25, 1998.
McWatters et al., *Nature*, 408:716-720, 2000.
Mizoguchi et al., *Dev. Cell*, 2:629-641, 2002.
Mouradov et al., *Plant Cell*, S111-S130, 2002.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11(7):471-473, 1997.
Nelson et al., *Cell* 101:331-340, 2000.
Odell et al., *Nature*, 313:810-812, 1985.
Ogawa et al., *Sci. Rep.*, 13:42-48, 1973.
Omirulleh et al., *Plant Mol. Biol.*, 21(3):415-428, 1993.
Onouchi et al., *Plant Cell*, 12:885-900, 2000.
Ow et al., *Science*, 234:856-859, 1986.
Park et al., *Science*, 285:1579-1582, 1999.
PCT App. WO 92/17598
PCT App. WO 94/09699
PCT App. WO 95/06128
PCT App. WO 97/4103
PCT App. WO 97/41228
Potrykus et al., *Mol. Gen. Genet.*, 199:183-188, 1985.
Prasher et al., *Biochem. Biophys. Res. Commun.*, 126(3):1259-1268, 1985.
Putterill et al., *Cell*, 80:847-857, 1995.
Reeves and Coupland, *Curr. Opin. Plant Biol.*, 3(1):37-42, 2000.
Reichel et al., *Proc. Natl. Acad. Sci. USA*, 93(12)5888-5893. 1996.
Rhodes et al., *Methods Mol. Biol.*, 55:121-131, 1995.
Ritala et al., *Plant Mol. Biol.*, 24(2):317-325, 1994.
Robson et al., *Plant Journal*, 28:619-631, 2001.
Rogers et al., *Methods Enzymol.*, 153:253-277, 1987.
Samach and Coupland, *Bioessays*, 22:38-47, 2000.
Samach et al., *Science*, 288:1613-1616, 2000.
Sambrook et al., In: *Molecular Cloning-A Laboratory Manual*, Cold Spring Harbour Laboratory Press, 2001.
Searle and Coupland, *EMBO J.*, 23(6):1217-1222, 2004.
Sheen et al., *Plant Journal*, 8(5):777-784, 1995.
Simpson et al., *Bioessays* 25:829-832, 2003.
Simpson and Dean, *Science*, 296:285-289, 2002.
Simpson et al., *Cell*, 113(6):777-787, 2003.
Singsit et al., *Transgenic Res.*, 6(2):169-176, 1997.
Spangenberg et al., *J. Plant Physiol.*, 145:693-701, 1995.
Spencer et al., *Plant Mol. Biology*, 18:201-210, 1992.
Stalker et al., *Science*, 242:419-422, 1988.
Suárez-López, et al., *Nature*, 410:1116-1120, 2001.
Sullivan et al., *Mol. Gen. Genet.*, 215(3):431-440, 1989.
Sutcliffe, *Proc. Natl. Acad. Sci. USA*, 75:3737-3741, 1978.
Thillet et al., *J. Biol. Chem.*, 263:12500-12508, 1988.
Thomas et al., *Plant Sci.* 69:189-198, 1990.
Thompson et al., *EMBO Journal*, 6(9):2519-2523, 1987.
Thompson et al., *Euphytica*, 85(1-3):75-80, 1995.
Tian et al., *Plant Cell Rep.*, 16:267-271, 1997.
Tingay et al., *Plant Journal*, 11(6):1369-1376. 1997.
Tomes et al., *Plant. Mol. Biol.* 14(2):261-268, 1990.
Torbet et al., *Crop Science*, 38(1):226-231, 1998.
Torbet et al., *Plant Cell Reports*, 14(10):635-640, 1995.
Tsukada et al, *Plant Cell Physiol.*, 30(4)599-604, 1989.
Uchimiya et al., *Mol. Gen. Genet.*, 204:204, 1986.
Valverde et al., *Science*, 303:1003-1006, 2004.
Van Eck et al., *Plant Cell Reports*, 14(5):299-304, 1995.
Vasil et al., *Plant Physiol.*, 91:1575-1579, 1989.
Walker et al., *Proc. Natl. Acad. Sci. USA*, 84:6624-6628, 1987.
Wang and Tobin, *Cell*, 93:1207-1217, 1998.
Wang et al., *Molecular and Cellular Biology*, 12(8):3399-3406, 1992.
Yang and Russell, *Proc. Natl. Acad. Sci. USA*, 87:4144-4148, 1990.
Yanovsky and Kay, *Nature*, 419:308-312, 2002.
Zhou et al., *Plant Cell Reports*, 12(11).612-616, 1993.
Zukowsky et al., *Proc. Natl. Acad. Sci. USA*, 80:1101-1105, 1983.

What is claimed is:

1. An isolated nucleic acid sequence operably linked to a heterologous promoter, wherein the isolated nucleic acid sequence is selected from the group consisting of:
   (a) a nucleic acid sequence encoding the polypeptide of SEQ ID NO:2;
   (b) a nucleic acid sequence comprising the sequence of SEQ ID NO: 1;
   (c) a nucleic acid sequence encoding a polypeptide with at least 90% sequence identity to SEQ ID NO:2, wherein ectopic expression of said nucleic acid in a plant causes said plant to have delayed flowering compared to a control plant and;
   (d) the complement of the sequence of any of (a)-(c).

2. A recombinant vector comprising the isolated nucleic acid sequence of claim 1.

3. The recombinant vector of claim 2, further comprising at least one additional sequence chosen from the group consisting of: a regulatory sequence, a selectable marker, a leader sequence and a terminator.

4. The recombinant vector of claim 3, wherein the additional sequence is a heterologous sequence.

5. The recombinant vector of claim 2, wherein the promoter is a developmentally-regulated, organelle-specific, inducible, tissue-specific, constitutive, cell-specific, seed specific, or germination-specific promoter.

6. The recombinant vector of claim 2, defined as an isolated expression cassette.

7. A transgenic plant transformed with a selected DNA comprising the nucleic acid sequence of claim 1.

8. The transgenic plant of claim 7, further defined as an $R_0$ transgenic plant.

9. The transgenic plant of claim 7, further defined as a progeny plant of any generation of an $R_0$ transgenic plant, wherein said transgenic plant has inherited said selected DNA from said $R_0$ transgenic plant.

10. A seed of the transgenic plant of claim 7, wherein said seed comprises said selected DNA.

11. A host cell transformed with a selected DNA comprising the nucleic acid sequence of claim 1, wherein the host cell is a bacterial or plant cell.

12. The host cell of claim 11, wherein said host cell expresses a protein encoded by said selected DNA.

13. The host cell of claim 11, wherein the cell has inherited said selected DNA from a progenitor of the cell.

14. The host cell of claim 11, wherein the cell has been transformed directly with said selected DNA.

15. The host cell of claim 11, wherein said host cell is a plant cell.

16. A method of delaying flowering in a plant comprising introducing into the plant the isolated nucleic acid sequence of claim 1, wherein the nucleic acid is expressed in the plant to delay flowering relative to a plant of the same genotype that lacks the isolated nucleic acid.

17. The method of claim 16, wherein the isolated nucleic acid sequence is from a species selected from the group consisting of: *Arabidopsis thaliana,* barley, cotton, grape, maize, potato, rice, sugarcane, sorghum, soybean, tomato, wheat and *Medicago truncatula.*

18. The method of claim 16, wherein introducing the isolated nucleic acid comprises plant breeding.

19. The method of claim 16, wherein introducing the isolated nucleic acid comprises genetic transformation.

* * * * *

UNITED STATES PATENT AND TRADEMARK OFFICE
CERTIFICATE OF CORRECTION

PATENT NO.       : 7,572,953 B2
APPLICATION NO.  : 11/211148
DATED            : August 11, 2009
INVENTOR(S)      : Cheng et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 419 days.

Signed and Sealed this

Seventh Day of September, 2010

David J. Kappos
*Director of the United States Patent and Trademark Office*

SEQUENCE LISTING

<160> NUMBER OF SEQ ID NOS: 37

<210> SEQ ID NO 1
<211> LENGTH: 1119
<212> TYPE: DNA
<213> ORGANISM: Arabidopsis thaliana

```
<220> FEATURE:
<221> NAME/KEY: CDS
<222> LOCATION: (1)..(1119)

<400> SEQUENCE: 1 atg ggt tac atg tgt gac ttc tgt ggt gaa caa aga tct atg gtg tac      48
Met Gly Tyr Met Cys Asp Phe Cys Gly Glu Gln Arg Ser Met Val Tyr
 1               5                  10                  15 tgt cga tcc gat gca gct tgt ttg tgt ctc tcc tgt gac cgg agt gtt      96
Cys Arg Ser Asp Ala Ala Cys Leu Cys Leu Ser Cys Asp Arg Ser Val
             20                  25                  30 cat tcc gct aat gca ttg tcc aaa cga cat tct cgg aca ctt gtc tgc     144
His Ser Ala Asn Ala Leu Ser Lys Arg His Ser Arg Thr Leu Val Cys
         35                  40                  45 gag aga tgc aat gct cag cct gct act gtc agg tgt gtt gaa gaa agg     192
Glu Arg Cys Asn Ala Gln Pro Ala Thr Val Arg Cys Val Glu Glu Arg
     50                  55                  60 gtt tca ctc tgt caa aac tgt gac tgg tct ggc cac aac aac agc aac     240
Val Ser Leu Cys Gln Asn Cys Asp Trp Ser Gly His Asn Asn Ser Asn
 65                  70                  75                  80 aac aac aat tct tcg tct tct tct act tcg ccg cag cag cat aag agg     288
Asn Asn Asn Ser Ser Ser Ser Ser Thr Ser Pro Gln Gln His Lys Arg
                 85                  90                  95 caa acc ata agt tgc tat tcg ggt tgc cct tcc agc tca gaa ctc gct     336
Gln Thr Ile Ser Cys Tyr Ser Gly Cys Pro Ser Ser Ser Glu Leu Ala
            100                 105                 110 tcc att tgg tct ttc tgt ttg gac tta gct gga caa tct att tgt gaa     384
Ser Ile Trp Ser Phe Cys Leu Asp Leu Ala Gly Gln Ser Ile Cys Glu
        115                 120                 125 caa gaa ctg ggt atg atg aat ata gac gat gat ggt cct acc gac aag     432
Gln Glu Leu Gly Met Met Asn Ile Asp Asp Asp Gly Pro Thr Asp Lys
    130                 135                 140 aaa act tgt aat gag gat aag aaa gat gtc ttg gtt gga tcc tct tca     480
Lys Thr Cys Asn Glu Asp Lys Lys Asp Val Leu Val Gly Ser Ser Ser
145                 150                 155                 160 att cct gaa acc agt tct gta cca caa gga aaa tca tct tct gct aag     528
Ile Pro Glu Thr Ser Ser Val Pro Gln Gly Lys Ser Ser Ser Ala Lys
                165                 170                 175 gat gtt gga atg tgt gaa gat gac ttc tac ggg aac ctt ggt atg gat     576
Asp Val Gly Met Cys Glu Asp Asp Phe Tyr Gly Asn Leu Gly Met Asp
            180                 185                 190 gaa gtt gac atg gca ctt gag aac tat gaa gaa ctc ttt ggt acc gcc     624
Glu Val Asp Met Ala Leu Glu Asn Tyr Glu Glu Leu Phe Gly Thr Ala
        195                 200                 205 ttt aac ccc tct gaa gag cta ttc ggg cat ggt gga atc gat agc ctt     672
Phe Asn Pro Ser Glu Glu Leu Phe Gly His Gly Gly Ile Asp Ser Leu
    210                 215                 220 ttc cat aag cac caa aca gct cca gag gga ggg aat tcg gtg cag cca     720
Phe His Lys His Gln Thr Ala Pro Glu Gly Gly Asn Ser Val Gln Pro
225                 230                 235                 240 gca ggc agt aat gat tcg ttc atg agt tcg aaa act gag cca ata att     768
Ala Gly Ser Asn Asp Ser Phe Met Ser Ser Lys Thr Glu Pro Ile Ile
                245                 250                 255 tgc ttc gca tcg aag cca gca cat tcg aac ata tcc ttc tct gga gtc     816
Cys Phe Ala Ser Lys Pro Ala His Ser Asn Ile Ser Phe Ser Gly Val
            260                 265                 270 act gga gaa agt agt gct gga gat ttc caa gaa tgt ggt gca tca tct     864
Thr Gly Glu Ser Ser Ala Gly Asp Phe Gln Glu Cys Gly Ala Ser Ser
        275                 280                 285
```

```
tcc ata cag ctc tcg ggg gag cca cca tgg tat cct cca aca tta cag        912
Ser Ile Gln Leu Ser Gly Glu Pro Pro Trp Tyr Pro Pro Thr Leu Gln
    290                 295                 300 gat aac aat gcc tgc tca cat tca gta acc cgt aat aac gca gtt atg        960
Asp Asn Asn Ala Cys Ser His Ser Val Thr Arg Asn Asn Ala Val Met
305                 310                 315                 320 cgt tac aag gag aag aag aag gct cgc aag ttt gat aag aga gtg agg       1008
Arg Tyr Lys Glu Lys Lys Lys Ala Arg Lys Phe Asp Lys Arg Val Arg
                325                 330                 335 tat gct tcc cgc aaa gca aga gct gat gtg aga cgg cgt gta aag ggg       1056
Tyr Ala Ser Arg Lys Ala Arg Ala Asp Val Arg Arg Arg Val Lys Gly
            340                 345                 350 cga ttt gtc aaa gct ggt gaa gct tat gat tac gac cct ctc acc cca       1104
Arg Phe Val Lys Ala Gly Glu Ala Tyr Asp Tyr Asp Pro Leu Thr Pro
        355                 360                 365 acc aga agt tat tga                                                    1119
Thr Arg Ser Tyr
    370

<210> SEQ ID NO 2
<211> LENGTH: 372
<212> TYPE: PRT
<213> ORGANISM: Arabidopsis thaliana

<400> SEQUENCE: 2

Met Gly Tyr Met Cys Asp Phe Cys Gly Glu Gln Arg Ser Met Val Tyr
1               5                   10                  15

Cys Arg Ser Asp Ala Ala Cys Leu Cys Leu Ser Cys Asp Arg Ser Val
            20                  25                  30

His Ser Ala Asn Ala Leu Ser Lys Arg His Ser Arg Thr Leu Val Cys
        35                  40                  45

Glu Arg Cys Asn Ala Gln Pro Ala Thr Val Arg Cys Val Glu Glu Arg
    50                  55                  60

Val Ser Leu Cys Gln Asn Cys Asp Trp Ser Gly His Asn Asn Ser Asn
65                  70                  75                  80

Asn Asn Asn Ser Ser Ser Ser Thr Ser Pro Gln Gln His Lys Arg
                85                  90                  95

Gln Thr Ile Ser Cys Tyr Ser Gly Cys Pro Ser Ser Glu Leu Ala
            100                 105                 110

Ser Ile Trp Ser Phe Cys Leu Asp Leu Ala Gly Gln Ser Ile Cys Glu
        115                 120                 125

Gln Glu Leu Gly Met Met Asn Ile Asp Asp Gly Pro Thr Asp Lys
    130                 135                 140

Lys Thr Cys Asn Glu Asp Lys Lys Asp Val Leu Val Gly Ser Ser Ser
145                 150                 155                 160

Ile Pro Glu Thr Ser Ser Val Pro Gln Gly Lys Ser Ser Ala Lys
                165                 170                 175

Asp Val Gly Met Cys Glu Asp Asp Phe Tyr Gly Asn Leu Gly Met Asp
            180                 185                 190

Glu Val Asp Met Ala Leu Glu Asn Tyr Glu Glu Leu Phe Gly Thr Ala
        195                 200                 205

Phe Asn Pro Ser Glu Glu Leu Phe Gly His Gly Gly Ile Asp Ser Leu
    210                 215                 220

Phe His Lys His Gln Thr Ala Pro Glu Gly Gly Asn Ser Val Gln Pro
225                 230                 235                 240

Ala Gly Ser Asn Asp Ser Phe Met Ser Ser Lys Thr Glu Pro Ile Ile
                245                 250                 255
```

-continued

```
Cys Phe Ala Ser Lys Pro Ala His Ser Asn Ile Ser Phe Ser Gly Val
            260                 265                 270

Thr Gly Glu Ser Ser Ala Gly Asp Phe Gln Glu Cys Gly Ala Ser Ser
        275                 280                 285

Ser Ile Gln Leu Ser Gly Glu Pro Pro Trp Tyr Pro Thr Leu Gln
    290                 295                 300

Asp Asn Asn Ala Cys Ser His Ser Val Thr Arg Asn Asn Ala Val Met
305                 310                 315                 320

Arg Tyr Lys Glu Lys Lys Ala Arg Lys Phe Asp Lys Arg Val Arg
            325                 330                 335

Tyr Ala Ser Arg Lys Ala Arg Ala Asp Val Arg Arg Val Lys Gly
            340                 345                 350

Arg Phe Val Lys Ala Gly Glu Ala Tyr Asp Tyr Asp Pro Leu Thr Pro
            355                 360                 365

Thr Arg Ser Tyr
    370

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
tcaccaccaa agcgagaaaa                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
tggcttgcag ggtcaggttg                                                     20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 5
gcggcgaaga tagcggagtt aggt                                                24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 6
gttgccgtta tccatcccgt cgtc                                                24
```

```
<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
ttctccaaac gtcgcaacgg tct                                          23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gatttgtcca gcaggtgaca tctc                                         24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tagtaagcag agttgttgga gacg                                         24

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gggaaggccg agattgtaga t                                            21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
ctttctttct tcttctccct ccag                                         24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
ttgctcgaat acatttgaca cttt                                         24
```

```
<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
gtgttgcgtc tgcgtggagg ta                                              22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ttgtcattag aaagaaagag ata                                             23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
ttctcgagat gggttacatg tgt                                             23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
tgtctagatc aataacttct ggtt                                            24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
ctctagaaaa attaacactt gctca                                           25

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
accatggcct tcttgtggac tactactat                                       29
```

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic Primer

<400> SEQUENCE: 19
gccgcaactt tcgcctcatc at                                           22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic Primer

<400> SEQUENCE: 20
tgcatccgcc tcaacatcat cac                                          23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic Primer

<400> SEQUENCE: 21
agttgagtac cggtgctttg tcg                                          23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic Primer

<400> SEQUENCE: 22
ccgcctccac cagatccgta acct                                         24

<210> SEQ ID NO 23
<211> LENGTH: 1037
<212> TYPE: DNA
<213> ORGANISM: Wheat
<220> FEATURE:
<221> NAME/KEY: modified_base
<222> LOCATION: (835)..(1028)
<223> OTHER INFORMATION: n = a, c, g or t/u

<400> SEQUENCE: 23
tccacacgtt cagacagagc aactatttga tgatgctgga attgacagtt tctttgaatt    60
gaaggaaatg ccagctgctg attgtgacca gcagctcaac cccatgcgac ccaaatgtag   120
caacgcggta tctgctgatt ccagtctttg tgttcctgca aggcaggcca tatctactat   180
ttccctctcg ttctctggtt tgactggtga gagcaatgct ggagatcacc aagattgtga   240
ggtatcacca ctgctcctta tgggcgagca accctggctt cctcctggtt ctgaaggatc   300
atctgccggt ggtagcagag gtagcgctct ctcacggtac atggagaaga agaagagaag   360
aaaattcgac aagaagatca ggtacgcttc tcgcaaggcc agggcagacg tgaggaagag   420
ggtcaagggc cggttcgtga aagcgggcga agcatacgac tacgatccgc tcagcgacac   480

-continued

```
acgaagctac tgaagcccaa acgccattgg caatatcatc cagtgtcaga ctagcaacaa    540
ttataaactt gagcagctca tgtggtgttg ctcgcactaa gcaagagcgc atgcagggga    600
gcactagcac ttgtgccgga cagcgcaacc ggaaaaagcg ctaaaaaaca caccagctgg    660
tgagttggaa aatactacag atagagaagc tgcaaatacg caggaatcca tgctatgccg    720
ctgctccatt ttctttctcc ttggaagtgg acggagcgtg cgtgcatata cattccttcc    780
tgggtggtgg gttccgttaa tctccaacat ctgcgcatta tccaatacga ttacanggac    840
tatctcccaa ctcacaacca acgcatgcgt gggatatact gccacgctcc gtgtcngtgc    900
gctggtgcaa gtcctgataa ttatctcgtg tgctagttct ctgtgaatat tgttanacca    960
gngctggaac ctgtttaaac aactngggct tgtaactgta atcgtccgta ttaaancggt   1020
ataatgantc aaaaaaa                                                  1037

<210> SEQ ID NO 24
<211> LENGTH: 1152
<212> TYPE: DNA
<213> ORGANISM: Barley

<400> SEQUENCE: 24
atgggtgctc tctgcgatta ctgtggggag cataggtcca tggtttactg ccgatccgat     60
gcagcctctt tgtgcttgtc atgcgaccgc aatgtgcatt cagctaatgc tctttctcgg    120
cgccatacaa gaacccttct atgtgaccgg tgtgcttcac agcctgccat ggtccgctgc    180
ctagaagaga cacctcact ttgccaaaat tgtgactgga atgggcatag tgctggatcc    240
tccgctgctg gacacaaaag acagaatata aactgctatt cggggtgccc atcatctgca    300 gagcttttcaa gaatgtggtc attcattttg gatattccta atgtagctcc tgagctgaat    360
tgtgagcaag taataagcat gatgagcatc agtgacagtg ctgtcagtaa tggagacaat    420
gctcaagggg acaacagttt ggtagatatg gcttgtgcaa cacttgatga agaagacaag    480
caaaagtctg tgatcggctc atcttccgaa gctggtctga accttcttcc acctactaat    540
gatcagacag ctgtatctgt ggattcgacg acacctaagt atacgccaga caagcatatg    600
ttcagcaagg atagcatata tgaagatttc tctatggatg atattgatct gagttacgaa    660
aactatgaag aactgtttgg tactcctcac attcagacag agcaactatt tgatgatgct    720
ggaattgaca gctactttgg aatgaaggaa atgccagctg ctgattgtaa cgagcagctc    780
aaacccatgc agcccgaatg tagcaacgcg gtatctgctg actccagcct ctgtgttcct    840
gctaggcagg ccatatccag tatttccctc tcgttctctg gtttcaccgg cgagggcaat    900
gctggagatc accaagattg tggggtatca ccctggcttc atcctggtcc tgaaggttca    960
tctgccagtg gtagcagagg tagtgctctc tcgcggtaca tggagaagaa gaagagaaga   1020
aaattcgaca agaagatcag gtacgcttct cgcaaggcta gggcagacgt gaggaaaagg   1080
gtcaagggcc ggtttgtgaa agcgggcgaa gcatacgact atgatccact ctgcgataca   1140
cgaagctact ga                                                       1152

<210> SEQ ID NO 25
<211> LENGTH: 705
<212> TYPE: DNA
<213> ORGANISM: Cotton

<400> SEQUENCE: 25
ctggaccagc cagctggacc taccaatgaa tgtctgccaa agttatactg tcctgctaca     60
aaatgccctg ccttatctga agatgataat ctgtatgatg atttcaacat ggatgaagtg    120
```

-continued

```
gatctagatc ttgagaacta tgaagaactt tttggtatgg ccctcagtca ttctgaggag    180 cttttttgaaa atggtggaat tgatagcttg tttgggacaa aaggcatgtc tgctggagat    240
tccaattgtc aggaagctat tgctgctgag gggtcgtcgg ttggacaggt caatgcaatg    300
caaccagctt gcagcaatgc agcgtctgca gattccattt tgagtactaa aactgaacca    360
attctttgtt ttactggaag gcaaactcaa tcaaaccttt cttttctgg tgttactgga     420 gacagtagtg ctggagacta tcaagactgt ggggcttctt caatgcttct catgggagaa    480
cctccttggt ttgctccttg tccggagaat tccctacaat cagccaaccg tagtaatgct    540
gtcatgcggt acaaggaaaa gaagaagaca cggatgtttg acaaaaaagt gaggtatgcc    600
tctcgcaagg caagggctga tgtcagaagg cgcgtgaaag gccggtttgt caaagccggt    660
gacgtctacg attatgaccc tttgagcaca accagaagct gctga                    705
```

<210> SEQ ID NO 26
<211> LENGTH: 1191
<212> TYPE: DNA
<213> ORGANISM: Lolium

<400> SEQUENCE: 26

```
atgggcgctc tctgcgatta ctgcggggag cataggtcca tggtttactg ccgatcggat    60
tctgcagctc tgtgcttgtc atgtgaccgc aacgtgcatt cagccaacgc tctttctcgg    120
cgccattcaa gaaccctctct atgtgaccgg tgttctgcac agcctgccat ggtccgctgc    180
ctagaagaga acgcctcgct tgccaaaaat tgcgactgga atgggcatag tgctggatcg    240
tccgctgctg ccacaacag acagaatata aattgctatt caggatgccc atcatctgca    300 gagcttttcga gagtctggtc atttattttg gatattcctg atgtagctcc cgagccaaac    360
tgtgagcaaa taataagcat gatgagcatc agtgaaagtg ttgtcagtaa cggagacaat    420
gctcaagggg acaacacttt gttggatatg caagcgcaa caattaccaa taatcttaat    480
aatgaagaca agcaaaagtc tgtgatgggc ccatctttttg aagctggtcc ggaccttctt    540
ccacttgcta atgatcaggt agccgtatct gtggattcga cgacagctaa gtatacacca    600
gacaaacata tgttcagcaa caaggacagc atatatgaag atttctcaat ggatgatatt    660
gacctgagtt acgaaaatta tgaagaacta tttggtaact ctcatattca gactgaagaa    720 ctcttttgatg atgctgggat tgacagttac tttgaaatga aggaagtgca tgcagggagt    780
acagatgaga agcccaagcc gacaatgcca gctgtatctg ctgactctgg aatgtcaaat    840
ccaggaataa aagatgattc cagtctttgc atccctgtta ggcaagctat ttcctattct    900
ggctttactg gtgagagcat tcctgcagaa taccaggatt gtggggtatc accaatgctc    960
cttatgggtg agcctccttg gcttcctcct ggccctgact gctcatttgc cggaattaga   1020
gatagtgcga ttacacggta caaggagaag aagaagagaa gaaaatttga ccacaagatc   1080
agatacgagt ctcgcaaggc cagggcggat gtgagaaaaa gagtgaaggg gcggttcgtt   1140
aaggctggtg aagcatatga ttatgatccg ctcgacacaa ggagctactg a            1191
```

<210> SEQ ID NO 27
<211> LENGTH: 498
<212> TYPE: DNA
<213> ORGANISM: Maize

<400> SEQUENCE: 27

```
gacgctggaa ttgacggtta cttcgaattg aaagagacac cacctttttta tttcaacgag    60 cagcccaaag ctatgcagat agaatgtggc aacgtggtat cagctgattg tgcgatgtca   120
```

```
aacccagggg caagggctga ttccagcctt tgtattcccg tcaggcaggt cagatctagt    180
atatcccact ccttatctgg tctgactggt gagagcagcg ctggagatca ccacgactgt    240
ggggtgtcac cgatgctcct catgggtgag ccaccctggc attcctctgg tggtccagaa    300
ggctcagtcg ctggaggcag cagagatagc gctctcacac ggtacaagga gaagaagaag    360
aggagaaagt tgacaagaa gatcagatat gcttctcgca aggctagggc ggacgtgagg     420
aagcgggtca agggacggtt cataaaggcc ggtgaagcgt acgactatga tccgctaagc    480
cagactagaa gctactga                                                  498
```

<210> SEQ ID NO 28
<211> LENGTH: 508
<212> TYPE: DNA
<213> ORGANISM: Medicago truncatula

<400> SEQUENCE: 28

```
gggcttattt ggggcaaaag ccatgtctgc cggagattcc aattgtcaag atgctaatgc     60
tgctgagggt tcatcaattg gacatgtcaa tgcagcacaa ccagcatgca gcactgcagc    120
atctgcagat tccatattga gtactaaaac tgaaccaaat cttttgtatta ctgcaaagca    180 atcccaatcg agccttttctt tttctggtat taatgaagac ggtggtgctg agactatca    240 agattgtgga gcttcttcaa tgcttctcat gggagaacct ccttggttaa acacttgtcc    300
tgagaatgag ctacaactac aatctgctaa ccgctgtagt gctgttatgc gatacaagga    360
aaagaaaaag acacgcaagt ttgacaaaag agtgagatat gcctctcgca aggaaagggc    420
tgatgtccga aggcgcgtga agggccggtt tgttaaagcc ggcgaggcct atgattatga    480
ccctttgagc caaaccagaa gctactga                                       508
```

<210> SEQ ID NO 29
<211> LENGTH: 1227
<212> TYPE: DNA
<213> ORGANISM: Potato

<400> SEQUENCE: 29

```
atgggttata tatgtgaata ctgtggagag caaagatcaa ttgtatattg ccggtctgat     60
gcagcttgtt tatgtttgtc gtgtgatcga aatgtccatt ctgcaaatgc cctttcacaa    120
cgtcattcca ggacacttat atgtgaaaga tgtaattcac aaccagctgt tgttagatgt    180
gttgaggaga gaacatctct ttgccagaac tgtgattggt caggtcatgc tagttctagt    240
tcaggttcat caatgcacaa gagacaagca cttagttgtt atacgggatg tccttccgct    300
gctgaacttt ctaatatctg gtcattttta ttagatgacc cttcaattgg tgatacttgt    360
gaacagagaa tgggttcaat gagcatcaat gataaccgtc ctagggatgg tcaagatcct    420
caaggaaagg acaactcaca aaatgtgtgt gctgcagtcg aagtgaacga catgaatatt    480
tcagaaaaat cgaatctttt agtggaatca tctatgccta cttttgacaa caagctgcat    540
aatgtggaac cacctattgg atcttcgtcg aagggctgct atatgggagc aaagggctct    600
agtttatttg aggaggatcc ttattgtgat aatctcatta tggatgcggt ggacttgagt    660 atttgagaatt atgaagagct atttggtgat tctctcaatt atccggatga gctatttgag    720
aatgaaaatt tggatagctt ctttgggatg aaggacataa aaggtgccga ctacagctac    780
cgtggtgtca atgctgccga ggggtcatca aattggcgtg tgaatacagt gcagccaaca    840
tgtagcgatg cagcatctgc agattccatg atgagctgca agacggattc tatccttttac    900 tttgctagac aatctagtct ctcagtttcc aaccaaactg gtggagaatg cagtgctgga    960
```

```
gatcaccaag actgtggagt ctccccgatg ctcctaatgg gcgagccacc atggtgtcct   1020
ccatgtactg aaatttcatc gacatcgact agcaggagca atgctgtgtt gcgctaccag   1080
gaaaaaaaga agacaaggaa atttgacaag cgagtgagat atgtttcccg taagggcaga   1140
gctgatgtca aaggcgtgt gaagggacgg tttatcaagg ctggtgatgc ttacgactat   1200
gatcctctcc cgaccagaag ctattga                                       1227

<210> SEQ ID NO 30
<211> LENGTH: 1224
<212> TYPE: DNA
<213> ORGANISM: Rice

<400> SEQUENCE: 30
atggatgctc tttgtgattt ctgcagggag caaaggtcaa tggtctattg ccgatcagat     60
gcagcatcct tgtgcttgtc gtgtgatcgt aatgtgcatt cagccaatgc cctttcccga    120
cgccatacaa gaacccttct tgtgatcgt tgtgttggac agcctgcagc agtccgttgt    180
cttgaagaga cacctcact ttgccaaaac tgtgactgga atggacatgg ggcagcatcc    240
tcagctgctg gcataaaaag gcagaccata aactgttact cggggtgccc atcgtcggca    300
gagctctcga aatctggtc ctttagtatg atatcccaa ctgtagctgc ggagccaaac    360
tgtgaggaag gaataaacat gatgagcatt aatgacaatg acgtcaataa ccattgtggt    420
gctccagaag atggccgctt gttggatata gctagcacag cactcatgag tgatttacct    480
acaggagaca agttcaaacc tttaataggt tcttcttcag gagatgggat gaatcttctg    540
ccacttaatt cagatcagcc agctgagcca gtttcaacga cgcctaaggc accctgtgtc    600
acagacaaag atatgttcaa tgatgggagc gtatatggag acttctgtgt ggatgatgct    660
gacctaacat ttgagaatta tgaagaatta ttcggtacct ctcacgttca aacagaacaa    720 ctcttttgatg atgctggaat tgacagttat tttgaaatga aggatgtgcc agcagatgaa    780
tctaatgagc agcccaaacc tgtgcagcca gaatgtagca atgtcgcatc tgttgattct    840
gggatgtcaa acccagctgc aagggctgat tccagccatt gtattcctgg taggcaggct    900
atatccaaca tatcccttc cttctctggt ttgactggtg aaagcagtgc tggatatttt    960
caagattgtg gggtatcgtc aatgatcctt atgggtgagc caccctggca tcctcctggt   1020
cctgaaagtt catctgctgg aggcagcaga gataatgctc ttacacggta caaggagaag   1080
aagaagagaa gaaatttga caagaagata aggtatgctt ctcgtaaggc tagggcagat   1140
gtgagaaaaa gggtcaaagg acggttgta aaggctggcg aagcatatga ctacgatccg   1200
ctgagccaaa caagaagcta ctaa                                         1224

<210> SEQ ID NO 31
<211> LENGTH: 1216
<212> TYPE: DNA
<213> ORGANISM: Sorghum

<400> SEQUENCE: 31
atggcctctc tttgtgattt ctgtgggaaa caaaggtcaa tgatctactg cagatcagat     60
gcggcatcat tgtgcttatc atgcgaccgt aatgttcatt cagctaatgc gctgtctcgg    120
cgtcatacaa ggacccttct tgtgatcgc tgtggttctc agcctgcatc agtcagatgt    180
cttgaggaca atgcatcact ttgccaaaac tgtgattgga atgggcatga tgcagcatca    240
ggggcttctg gcataaaaag gcaggctata aactgttact cagggtgccc atcatcagca    300
gagctttcaa gaatctggtc atttattatg gatatcccga ctgtacctgc tgagcccaac    360
```

```
tgtgaggatg gattaagcat gatgacaatt gatgacagcg atgtgactaa tcatcatgat      420
gcttcagatg ataaaagact gttggaaata gctaacacaa cactcatgag cgatccacct      480
tcagcagaca agcctaaacc tagagaagaa agtttgacaa gaagatcaga tatgcctcta      540
gccacagatc agcctgctgg atcagtttca gtgacaccta aggtacctta tgccagagat      600
gacgataatt tcaatgatgg catgtatgaa gacttatgtg tggatgatgc tgacatgaca      660
ttcgagaact atgaagagct atttggtacc tctcacattc gaacagagga actctttgat      720
gacgctggaa ttgacagtta ctttgaaatg aaggaaacac aaccttttga tttcaacgag      780
gagcccaaaa ctatgcagct agaatgtagc aatgtggtat cagctgattg tgggatgtta      840
aacccagggg caagggctga ttccagcctt tgtattcctg ttaggcaagt cagatctagt      900
atatcccatt ccctatctgg tttgactggt gagagcagcg ctggagatca ccaagattgt      960
ggggtgtcac caatgctcct catgggtgag cctccctggc attctcctgg tcctgaaggc     1020
tcagttgctg gaggcagcag agatagcgct ctcacacgat acaaggagaa gaagaagaga     1080
agaaagtttg acaagaagat cagatatgcc tctcgcaagg ctagggcaga cgtgaggaag     1140
agggtcaagg gacggtttat aaaggccggc gaagcatatg actatgatcc actaagccaa     1200
actagaagct actgag                                                     1216

<210> SEQ ID NO 32
<211> LENGTH: 705
<212> TYPE: DNA
<213> ORGANISM: Soybean

<400> SEQUENCE: 32
ctggaccagc cagctggacc taccaatgaa tgtctgccaa agttatactg tcctgctaca       60
aaatgccctg ccttatctga agatgataat ctgtatgatg atttcaacat ggatgaagtg      120
gatctagatc ttgagaacta tgaagaactt tttggtatgg ccctcagtca ttctgaggag      180 cttttttgaaa atggtggaat tgatagcttg tttgggacaa aaggcatgtc tgctggagat      240
tccaattgtc aggaagctat tgctgctgag gggtcgtcgg ttggacaggt caatgcaatg      300
caaccagctt gcagcaatgc agcgtctgca gattccattt tgagtactaa aactgaacca      360
attctttgtt ttactggaag gcaaactcaa tcaaaccttt cttttttctgg tgttactgga      420 gacagtagtg ctggagacta tcaagactgt ggggcttctt caatgcttct catgggagaa      480
cctccttggt ttgctccttg tccgagaat tccctacaat cagccaaccg tagtaatgct      540
gtcatgcggt acaaggaaaa gaagaagaca cggatgtttg acaaaaaagt gaggtatgcc      600
tctcgcaagg caagggctga tgtcagaagg cgcgtgaaag gccggtttgt caaagccggt      660
gacgtctacg attatgaccc tttgagcaca accagaagct gctga                     705

<210> SEQ ID NO 33
<211> LENGTH: 564
<212> TYPE: DNA
<213> ORGANISM: Tomato

<400> SEQUENCE: 33
atggggcata tgtgtgaatt ctgtggggag cagcggtcaa ttgtatattg ccggtctgat       60
gcagcttgct tatgtctgtc gtgtgattgc aatgtgcatt cggccaatgc cctttcacag      120
cgccattcca ggacactttt gtgcgaaaga tgtaattcac aaccagctat tgttagacgt      180
gttgaggaga aggtttctct ttgcaagaac tgtgattcga ttggtcatgc tggttctggt      240
acaggttcag tgcataatag acaagcactt agttcttata ctggatgccc ttctgctgca      300
```

| | | | |
|---|---|---|---|
| gaactctcta ctatctggtc gtttctctta gataattctt taggtggtga ttcaacttgt | 360 |
| gagaagggaa tgggttcaat gagcatcacc gataaccgtc ttacggatag ccgagctcct | 420 |
| caaggaaagt tcaactctca agatgcatct gctacagttg aagtgagtga aatacatacc | 480 |
| ccaggcaaat caagcatatt ggtgggatcc tctatgccta atcttggcaa caagctaaac | 540 |
| aaggtggagc atattgctgg atct | 564 |

<210> SEQ ID NO 34
<211> LENGTH: 1122
<212> TYPE: DNA
<213> ORGANISM: Arabidopsis thaliana

<400> SEQUENCE: 34

| | | | |
|---|---|---|---|
| atgggttata tgtgtgattt ctgtggtgaa caaagatcaa tggtgtattg tcgatctgat | 60 |
| gcagcgtgtt tgtgtctttc gtgtgaccgt aatgttcatt ctgctaatgc tctatcgaaa | 120 |
| cgtcattcgc ggactttggt atgtgagagg tgtaatgcac agccagcttc tgtccggtgt | 180 |
| agtgatgaga gggtttctct atgtcaaaac tgtgattggt caggccatga cggcaagaat | 240 |
| tctactacta cttcacatca taaaaggcaa accatcaatt gttattctgg ttgtccctcg | 300 |
| agtgccgaat tatcctcgat atggtctttc tgtatggatt tgaatatctc ttctgctgaa | 360 |
| gaatccgctt gtgagcaagg aatgggtttg atgactatag atgaagatgg cacaggagaa | 420 |
| aaatctggtg tccaaaaaat taatgtagaa cagcctgaaa ccagttcggc tgcacaaggt | 480 |
| atggatcact ctagtgttcc agaaaattca tcaatggcta aggagcttgg agtatgtgag | 540 |
| gatgacttca atggaaatct catttcagat gaagtagact tggctcttga aactatgaa | 600 |
| gaactctttg gttcagcctt caactcatca agatatctct tcgagcacgg tggaattgga | 660 |
| agtcttttcg agaaagatga agctcatgag ggctcaatgc agcagccagc attaagcaat | 720 |
| aatgcatctg cagattcgtt catgacttgt agaaccgagc caataatttg ctattcatca | 780 |
| aagccagcac attcgaatat ctccttctct ggcatcactg agaaagtaa tgctggagat | 840 |
| ttccaagatt gtggggcgtc atcgatgaag cagctttcaa gggagccaca accatggtgc | 900 |
| catccaacag cacaggacat tattgcttcc tcacatgcaa caacacgtaa taacgctgtt | 960 |
| atgcgttaca aggaaaagaa gaaggctcgc aagtttgaca agcgagtaag gtatgtctct | 1020 |
| aggaaagaaa gggctgatgt gagacggcgt gtgaaaggac ggtttgtcaa gtccggtgaa | 1080 |
| gcttatgatt acgacccgat gagcccaaca agaagctact ga | 1122 |

<210> SEQ ID NO 35
<211> LENGTH: 373
<212> TYPE: PRT
<213> ORGANISM: Arabidopsis thaliana

<400> SEQUENCE: 35

Met Gly Tyr Met Cys Asp Phe Cys Gly Glu Gln Arg Ser Met Val Tyr
1               5                   10                  15

Cys Arg Ser Asp Ala Ala Cys Leu Cys Leu Ser Cys Asp Arg Asn Val
            20                  25                  30

His Ser Ala Asn Ala Leu Ser Lys Arg His Ser Arg Thr Leu Val Cys
        35                  40                  45

Glu Arg Cys Asn Ala Gln Pro Ala Ser Val Arg Cys Ser Asp Glu Arg
    50                  55                  60

Val Ser Leu Cys Gln Asn Cys Asp Trp Ser Gly His Asp Gly Lys Asn
65                  70                  75                  80

Ser Thr Thr Thr Ser His His Lys Arg Gln Thr Ile Asn Cys Tyr Ser
            85                  90                  95

Gly Cys Pro Ser Ser Ala Glu Leu Ser Ser Ile Trp Ser Phe Cys Met
        100                 105                 110

Asp Leu Asn Ile Ser Ser Ala Glu Glu Ser Ala Cys Glu Gln Gly Met
            115                 120                 125

Gly Leu Met Thr Ile Asp Glu Asp Gly Thr Gly Glu Lys Ser Gly Val
        130                 135                 140

Gln Lys Ile Asn Val Glu Gln Pro Glu Thr Ser Ser Ala Ala Gln Gly
145                 150                 155                 160

Met Asp His Ser Ser Val Pro Glu Asn Ser Ser Met Ala Lys Glu Leu
                165                 170                 175

Gly Val Cys Glu Asp Asp Phe Asn Gly Asn Leu Ile Ser Asp Glu Val
            180                 185                 190

Asp Leu Ala Leu Glu Asn Tyr Glu Glu Leu Phe Gly Ser Ala Phe Asn
        195                 200                 205

Ser Ser Arg Tyr Leu Phe Glu His Gly Gly Ile Gly Ser Leu Phe Glu
    210                 215                 220

Lys Asp Glu Ala His Glu Gly Ser Met Gln Gln Pro Ala Leu Ser Asn
225                 230                 235                 240

Asn Ala Ser Ala Asp Ser Phe Met Thr Cys Arg Thr Glu Pro Ile Ile
                245                 250                 255

Cys Tyr Ser Ser Lys Pro Ala His Ser Asn Ile Ser Phe Ser Gly Ile
            260                 265                 270

Thr Gly Glu Ser Asn Ala Gly Asp Phe Gln Asp Cys Gly Ala Ser Ser
        275                 280                 285

Met Lys Gln Leu Ser Arg Glu Pro Gln Pro Trp Cys His Pro Thr Ala
    290                 295                 300

Gln Asp Ile Ile Ala Ser Ser His Ala Thr Thr Arg Asn Asn Ala Val
305                 310                 315                 320

Met Arg Tyr Lys Glu Lys Lys Lys Ala Arg Lys Phe Asp Lys Arg Val
                325                 330                 335

Arg Tyr Val Ser Arg Lys Glu Arg Ala Asp Val Arg Arg Val Lys
            340                 345                 350

Gly Arg Phe Val Lys Ser Gly Glu Ala Tyr Asp Tyr Asp Pro Met Ser
        355                 360                 365

Pro Thr Arg Ser Tyr
    370

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
gtagatctga tgggttatat gtgtga                                          26

<210> SEQ ID NO 37
<211> LENGTH: 28
<212> TYPE: DNA
<213> ORGANISM: Artificial Sequence

```
-continued

<220> FEATURE:
<223> OTHER INFORMATION: Description of Artificial Sequence:  Synthetic
      Primer

<400> SEQUENCE: 37
ggtcacctca gcttcttgtt gggctcat                                            28
```